United States Patent
Den Boef

(10) Patent No.: US 10,268,124 B2
(45) Date of Patent: Apr. 23, 2019

(54) ASYMMETRY MONITORING OF A STRUCTURE

(71) Applicant: ASML NETHERLANDS B.V., Veldhoven (NL)

(72) Inventor: Arie Jeffrey Den Boef, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/913,920

(22) Filed: Mar. 7, 2018

(65) Prior Publication Data

US 2018/0275524 A1    Sep. 27, 2018

Related U.S. Application Data

(60) Provisional application No. 62/475,679, filed on Mar. 23, 2017.

(51) Int. Cl.
*G03B 27/32* (2006.01)
*G03F 7/20* (2006.01)
(Continued)

(52) U.S. Cl.
CPC .......... *G03F 7/70625* (2013.01); *G01B 11/26* (2013.01); *G01N 21/9501* (2013.01);
(Continued)

(58) Field of Classification Search
CPC ............... G01B 11/26; G01B 9/02087; G01N 21/9501; G01N 21/956; G01N 21/95692;
(Continued)

(56) References Cited

U.S. PATENT DOCUMENTS

| 7,782,443 B2 | 8/2010 | Fiolka et al. |
| 7,791,732 B2 | 9/2010 | Den Boef et al. |

(Continued)

FOREIGN PATENT DOCUMENTS

| TW | 201535066 | 9/2015 |
| TW | 201631404 | 9/2016 |

(Continued)

OTHER PUBLICATIONS

Shapoval, Tetyana et al., "Etch process monitoring possibilities and root cause analysis", 27th Annual Semi Advanced Semiconductor Manufacturing Conference (ASMC), pp. 419-422 (May 2016).

(Continued)

*Primary Examiner* — Christina A Riddle
(74) *Attorney, Agent, or Firm* — Pillsbury Winthrop Shaw Pittman LLP

(57) ABSTRACT

A method including obtaining a first value of an optical characteristic determined for an etched profile of a substrate measured at a first wavelength of measurement radiation, obtaining a second value of the optical characteristic determined for the etched profile of the substrate measured at a second wavelength of measurement radiation, and obtaining a derived value that represents a difference between the first and second values; and determining, based on the first and second values or on the derived value, an occurrence of a tilt in the etching to form the etched profile.

19 Claims, 14 Drawing Sheets

(51) Int. Cl.
*G01B 11/26* (2006.01)
*G01N 21/95* (2006.01)

(52) U.S. Cl.
CPC .......... *G03F 7/705* (2013.01); *G03F 7/7065* (2013.01); *G03F 7/7085* (2013.01); *G03F 7/70516* (2013.01); *G03F 7/70616* (2013.01); *G03F 7/70633* (2013.01)

(58) Field of Classification Search
CPC ... G01N 21/95607; G01N 2021/95615; G01N 2021/95676; G01N 2021/213; G01N 2021/1748; G01N 2021/1753; H01L 22/10; H01L 22/12; H01L 22/20; H01L 22/24; H01L 22/26; G03F 7/70608; G03F 7/70616; G03F 7/70625; G03F 7/70633; G03F 7/70641; G03F 7/7065; G03F 7/70683; G03F 7/705; G03F 7/70516; G03F 7/7085; G03F 7/7055; G03F 7/706
USPC .............. 355/53, 52, 55, 67–71, 72, 77; 356/237.1, 237.2, 237.5, 601, 625, 626, 356/402, 407, 408, 630, 635; 216/59, 60, 216/67; 438/14, 16, 9; 702/155, 166, 702/167, 172
See application file for complete search history.

(56) References Cited

U.S. PATENT DOCUMENTS

| | | | | |
|---|---|---|---|---|
| 7,884,024 | B2* | 2/2011 | Le Roy | H01J 37/228 216/60 |
| 8,411,287 | B2 | 4/2013 | Smilde et al. | |
| 9,081,303 | B2 | 7/2015 | Cramer et al. | |
| 2002/0113966 | A1* | 8/2002 | Shchegrov | G01N 21/211 356/369 |
| 2002/0135781 | A1 | 9/2002 | Singh et al. | |
| 2004/0119971 | A1* | 6/2004 | Isozaki | G01N 21/9501 356/237.2 |
| 2006/0066855 | A1* | 3/2006 | Boef | G03F 7/70341 356/401 |
| 2007/0105029 | A1 | 5/2007 | Ausschnitt | |
| 2011/0027704 | A1 | 2/2011 | Cramer et al. | |
| 2011/0043791 | A1 | 2/2011 | Smilde et al. | |
| 2011/0080585 | A1 | 4/2011 | Rabello et al. | |
| 2012/0122252 | A1* | 5/2012 | Fujimori | G01N 21/95692 438/16 |
| 2012/0242940 | A1 | 9/2012 | Nagata et al. | |
| 2015/0176985 | A1* | 6/2015 | Shchegrov | H01L 22/12 356/614 |
| 2015/0227061 | A1* | 8/2015 | Tinnemans | G03F 9/7088 355/53 |
| 2016/0209755 | A1 | 7/2016 | Shmarev et al. | |
| 2016/0349627 | A1* | 12/2016 | Van Der Schaar | G03F 7/70633 |

FOREIGN PATENT DOCUMENTS

| | | |
|---|---|---|
| WO | 2009/078708 | 6/2009 |
| WO | 2009/106279 | 9/2009 |
| WO | 2011/012624 | 2/2011 |
| WO | 2014016056 | 1/2014 |
| WO | 2016083076 | 6/2016 |

OTHER PUBLICATIONS

Hwang, Stephen et al., "Evolution of across-wafer uniformity control in plasma etch", Solid State Technology, vol. 59, No. 5, pp. 16-20 (Jul. 2016).

Gatefait, Maxime et al., "Toward 7nm target on product overlay for C028 FDSOI technology", Proceedings of SPIE, vol. 8681, pp. 868105-1-868105-8 (2013).

Ruhm, Matthias et al., "Overlay leaves litho: impact of non-litho processes on overlay and compensation", Proceedings of SPIE, vol. 9231, pp. 92310O-1-92310O-10 (2014).

Leray, Philippe et al., "Improving scanner wafer alignment performance by target optimization", Proceedings of SPIE, vol. 9778, pp. 97782M-1-97782M-7 (Mar. 2016).

Kubis, Michael et al., "Ultimate intra-wafer critical dimension uniformity control by using lithography and etch tool corrections", Proceedings of SPIE, vol. 9780, pp. 978007-1-978007-8 (Mar. 2016).

Van Dijk, Leon et al., "Wafer-shape based in-plane distortion predictions using superfast 4G metrology", Proceedings of SPIE, vol. 10145, pp. 101452L-1-101452L-13 (Mar. 28, 2017).

Taiwanese Office Action issued in corresponding Taiwanese Patent Application No. 107109402, dated Oct. 17, 2018.

* cited by examiner

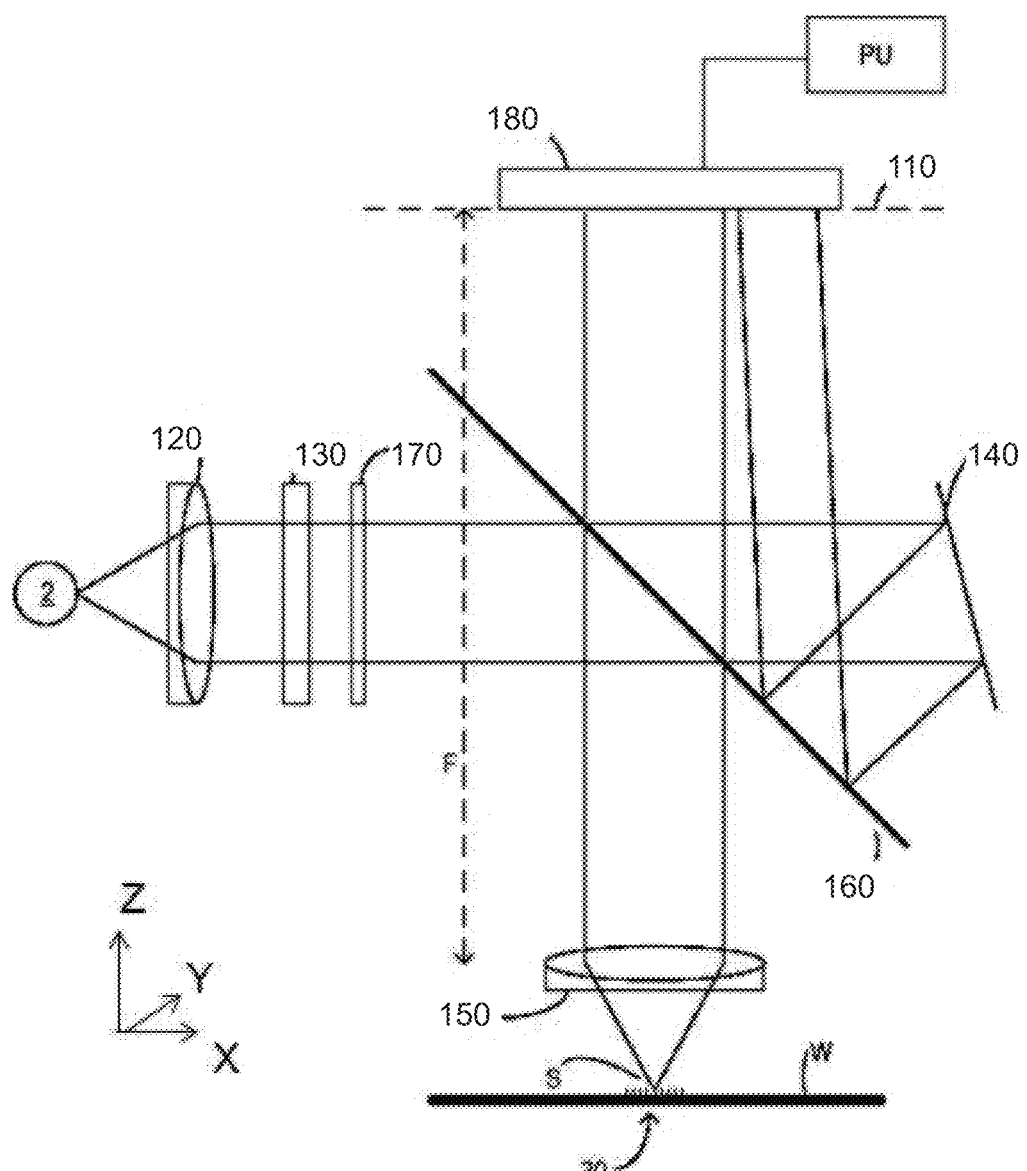
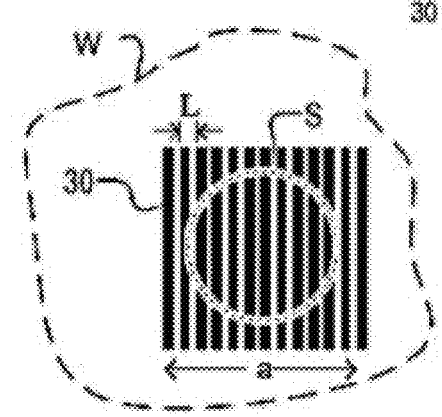
Fig. 4
Fig. 5

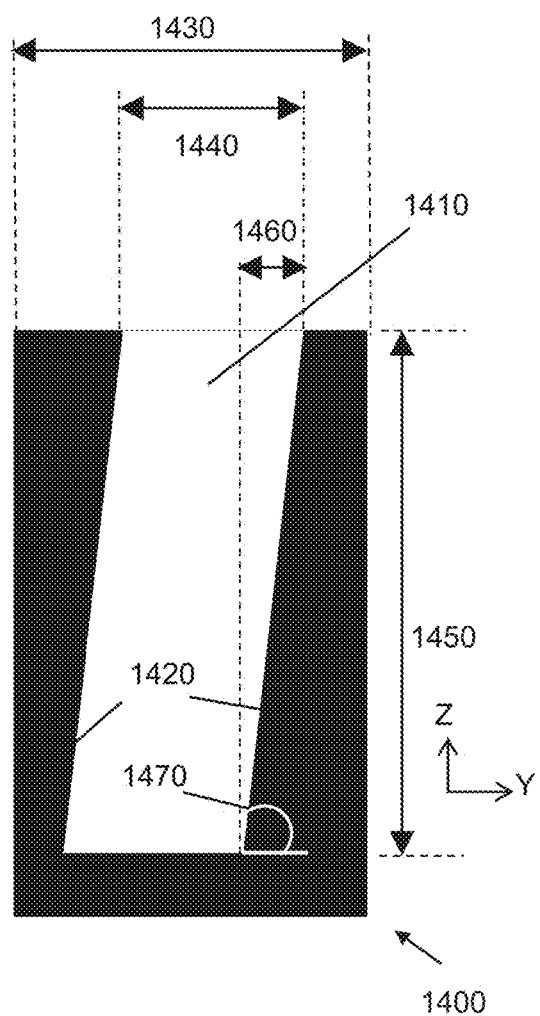
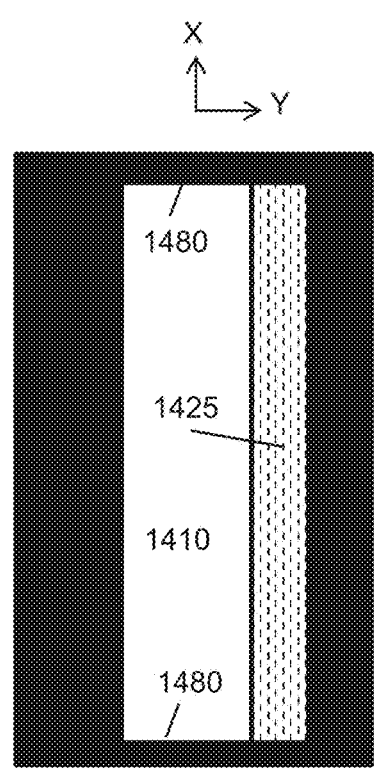
Fig. 11A
Fig. 11B

ASYMMETRY MONITORING OF A STRUCTURE

This application claims the benefit of priority of U.S. Provisional Patent Application No. 62/475,679, filed Mar. 23, 2017, which is incorporated by reference herein in its entirety.

FIELD

The present disclosure relates to methods and apparatus for inspection/metrology usable, for example, in the manufacture of devices by lithographic and etch techniques and to methods of manufacturing devices using lithographic and etch techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

Significant aspects to enabling a patterning process (i.e., a process of creating a device or other structure involving patterning (such as lithographic exposure or imprint), which may typically include one or more associated processing steps such as development of resist, etching, etc.) include developing the process itself, setting it up for monitoring and control and then actually monitoring and controlling the process itself. Assuming a configuration of the fundamentals of the patterning process, such as the patterning device pattern(s), the resist type(s), post-lithography process steps (such as the development, etch, etc.), it is desirable to setup the apparatus in the patterning process for transferring the pattern onto the substrates, develop one or more metrology targets to monitor the process, setup up a metrology process to measure the metrology targets and then implement a process of monitoring and/or controlling the process based on measurements.

So, in a patterning process, it is desirable to determine (e.g., measure, simulate using one or more models that model one or more aspects of the patterning process, etc.) one or more parameters of interest, such as the critical dimension (CD) of a structure, the overlay error between successive layers (i.e., the undesired and unintentional misalignment of successive layers) formed in or on the substrate, etc.

It is desirable to determine such one or more parameters of interest for structures created by a patterning process and use them for design, control and/or monitoring relating to the patterning process, e.g., for process design, control and/or verification. The determined one or more parameters of interest of patterned structures can be used for patterning process design, correction and/or verification, defect detection or classification, yield estimation and/or process control.

Thus, in patterning processes, it is desirable frequently to make measurements of the structures created, e.g., for process control and verification. Various tools for making such measurements are known, including scanning electron microscopes, which are often used to measure critical dimension (CD), and specialized tools to measure overlay, a measure of the accuracy of alignment of two layers in a device. Overlay may be described in terms of the degree of misalignment between the two layers, for example reference to a measured overlay of 1 nm may describe a situation where two layers are misaligned by 1 nm.

Various forms of inspection apparatus (e.g., metrology apparatus) have been developed for use in the lithographic field. For example, scatterometry devices direct a beam of radiation onto a target and measure one or more properties of the redirected (e.g., scattered) radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target by iterative approaches such as rigorous coupled wave analysis or finite element methods; library searches; and principal component analysis.

A further technique involves having the zeroth order of diffraction (corresponding to a specular reflection) blocked, and only higher orders are processed. Examples of such metrology can be found in PCT patent application publication nos. WO 2009/078708 and WO 2009/106279, which are hereby incorporated by reference in their entirety. Further developments of the technique have been described in U.S. patent application publication nos. US 2011-0027704, US 2011-0043791 and US 2012-0242940, each of which is incorporated herein in its entirety. Such diffraction-based techniques are typically used to measure overlay. The targets for techniques can be smaller than the illumination spot and may be surrounded by product structures on a substrate. A target can comprise multiple periodic structures, which can be measured in one image. In a particular form of such a metrology technique, overlay measurement results are obtained by measuring a target twice under certain conditions, while either rotating the target or changing the illumination mode or imaging mode to obtain separately the $-1^{st}$ and the $+1^{st}$ diffraction order intensities. The intensity asymmetry, a comparison of these diffraction order intensities, for a given target provides a measurement of target asymmetry, that is asymmetry in the target. This asymmetry in the target can be used as an indicator of overlay error.

SUMMARY

In the example of overlay measurement, the overlay measurement relies on an assumption that overlay (i.e., overlay error and deliberate bias) is the only cause of target asymmetry in the target. Any other asymmetry in the target, such as structural asymmetry of features within the periodic structure in an upper layer, within the periodic structure in a lower layer overlaid by the periodic structure in the upper layer, or both, also causes an intensity asymmetry in the $1^{st}$ (or other higher) orders. This intensity asymmetry attributable to such other asymmetry in the target, and which is not related to overlay (including an intentional bias), perturbs the overlay measurement, giving an inaccurate overlay measurement.

Asymmetry in the lower or bottom periodic structure of a target is a common form of structural asymmetry. It may originate, for example, in substrate processing steps performed to make the bottom periodic structure.

One example of a processing step that may cause structural asymmetry is etching. In particular, an etching process may have a tilt in the etching, such that, e.g., a trench is not aligned in a correct angular direction. In an embodiment, the tilt in the etching can be due to an ion beam tilt by which a trajectory of at least some of the ions of a plasma etch process is not perpendicular to the major surface of the substrate. The result is a slant of a surface in a trench (also referred to as sidewall angle) formed by the etching. This slant can cause an effective pattern shift from where the pattern was expected. Thus, it is desirable to be able to determine whether there is a structural asymmetry due to, e.g., tilt in the etching and signal the occurrence of such.

In an embodiment, there is provided a method comprising: obtaining a first value of an optical characteristic determined for an etched profile of a substrate measured at a first wavelength of measurement radiation, obtaining a second value of the optical characteristic determined for the etched profile of the substrate measured at a second wavelength of measurement radiation, and obtaining a derived value that represents a difference between the first and second values; and determining, by a hardware computer and based on the first and second values or on the derived value, an occurrence of a tilt in the etching to form the etched profile.

In an embodiment, there is provided a method, comprising: obtaining asymmetric optical characteristic values for an asymmetric etched profile of a substrate at each of a plurality of different wavelengths of measurement radiation, wherein the asymmetry of the etched profile is caused by tilt in the etching and each of the asymmetric optical characteristic values corresponds to a difference between a value of the optical characteristic for a first pupil location and a value of the optical characteristic for a second pupil location that is point symmetrically positioned with respect to a point at a central portion of the pupil; and identifying, by a hardware computer and based on the values, a first wavelength of measurement radiation at which a first value of the asymmetric optical characteristic values is negative and a second wavelength of measurement radiation at which a second value of the asymmetric optical characteristic values is positive, wherein occurrence of tilt in the etching of another etched profile can be determined by finding a difference between a value of the asymmetric optical characteristic determined for the other etched profile using a measurement at the first wavelength and a value of the asymmetric optical characteristic determined for the other etched profile using a measurement at the second wavelength.

In an embodiment, there is provided a metrology apparatus for measuring an object of a patterning process, the metrology apparatus configured to perform a method as described herein.

In an embodiment, there is provided a system comprising: a hardware processor system; and a non-transitory computer readable storage medium configured to store machine-readable instructions, wherein when executed, the machine-readable instructions cause the hardware processor system to perform a method as described herein.

In an embodiment, there is provided a computer program product comprising a computer non-transitory readable medium having instructions recorded thereon, the instructions when executed by a computer implementing a method as described herein.

In an embodiment, there is provided a system comprising: a metrology apparatus configured to provide a beam of radiation onto an object surface and to detect radiation redirected by the object surface; and a computer program product as described herein. In an embodiment, the system further comprises a lithographic apparatus comprising a support structure configured to hold a patterning device to modulate a radiation beam and a projection optical system arranged to project the modulated radiation beam onto a radiation-sensitive substrate, wherein the object is the substrate. In an embodiment, the system further comprises an etching apparatus configured to etch the object and having a control system configured to process a control signal derived from determination of the occurrence of a tilt in the etching.

Further features and advantages, as well as the structure and operation of various embodiments, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments will now be described, by way of example only, with reference to the accompanying drawings in which:

FIG. 4 schematically depicts an example inspection apparatus;

FIG. 5 illustrates the relationship between an illumination spot of an inspection apparatus and a metrology target;

FIG. 11A illustrates a highly schematic etched profile in cross-section from the side;

FIG. 11B illustrates a highly schematic etched profile from the top;

DETAILED DESCRIPTION

Before describing embodiments in detail, it is instructive to present an example environment in which embodiments may be implemented.

Figure 1:
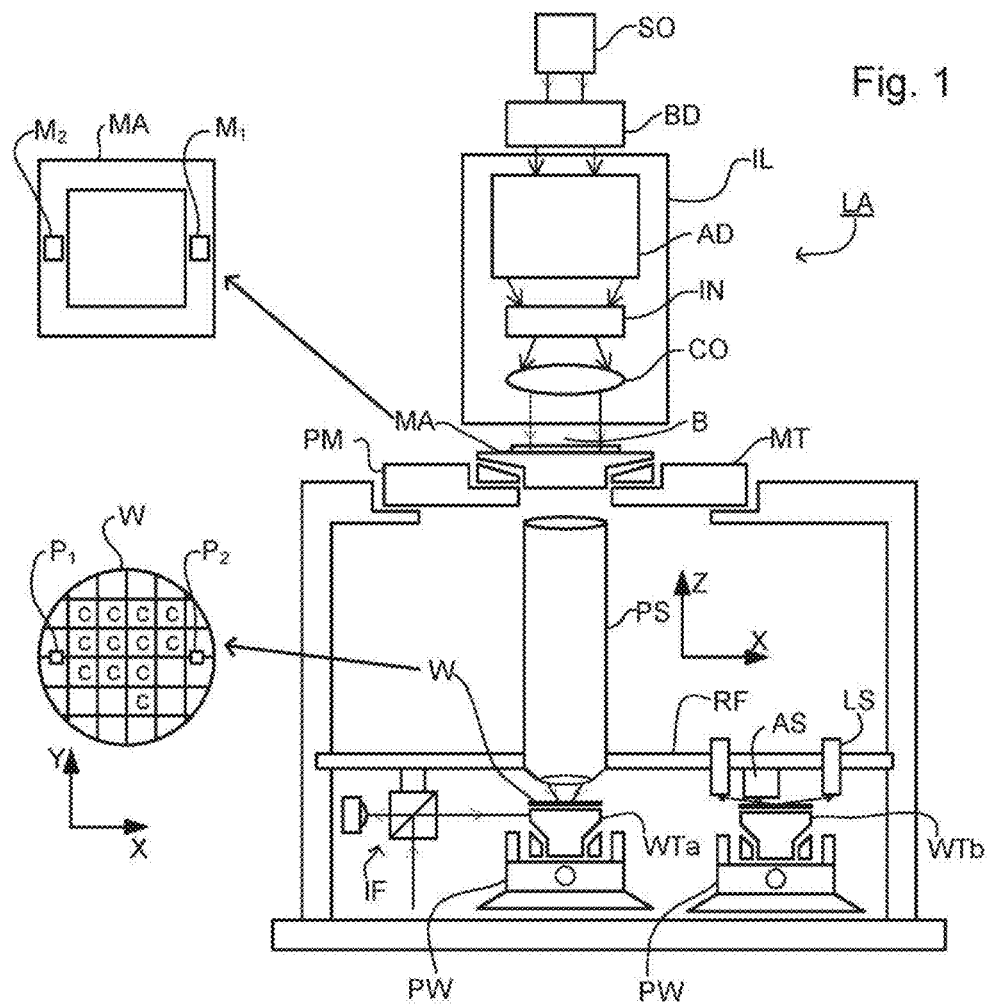
FIG. 1 depicts an embodiment of a lithographic apparatus.

FIG. 1 schematically depicts a lithographic apparatus LA. The apparatus includes an illumination optical system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection optical system (e.g., a refractive projection lens system) PS configured to project a pattern imparted to the radiation beam B by patterning device MA onto a target portion C (e.g., including one or more dies) of the substrate W.

The illumination optical system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly Interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table) MT, and is patterned by the patterning device. Having traversed the patterning device (e.g., mask) MA, the radiation beam B passes through the projection optical system PS, which focuses the beam onto a target portion C of the substrate W, thereby projecting an image of the pattern on the target portion C. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using patterning device alignment marks $M_1$, $M_2$ and substrate alignment marks $P_1$, $P_2$. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the patterning device alignment marks may be located between the dies. Small alignment markers may also be included within dies, in amongst the device features, in which case it is desirable that the markers be as small as possible and not require any different imaging or process conditions than adjacent features. The alignment system, which detects the alignment markers is described further below.

Lithographic apparatus LA in this example is of a so-called dual stage type which has two substrate tables WTa, WTb and two stations—an exposure station and a measurement station—between which the substrate tables can be exchanged. While one substrate on one substrate table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS. This enables a substantial increase in the throughput of the apparatus.

The depicted apparatus can be used in a variety of modes, including for example a step mode or a scan mode. The construction and operation of lithographic apparatus is well known to those skilled in the art and need not be described further for an understanding of the embodiments of the present invention.

Figure 2:
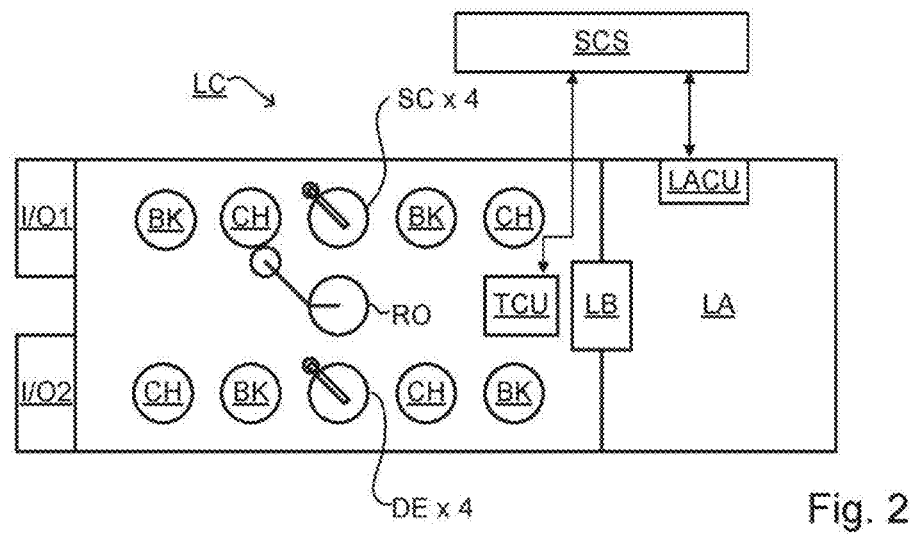
FIG. 2 depicts an embodiment of a lithographic cell or cluster.

As shown in FIG. 2, the lithographic apparatus LA forms part of a lithographic system, referred to as a lithographic cell LC or a lithocell or cluster. The lithographic cell LC may also include apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order to design, monitor, control, etc. the patterning process (e.g., a device manufacturing process) that includes at least one patterning step (e.g., an optical lithography step), the patterned substrate can be inspected and one or more parameters of the patterned substrate are measured. The one or more parameters may include, for example, overlay between successive layers formed in or on the patterned substrate, critical dimension (CD) (e.g., critical linewidth) of, for example, features formed in or on the patterned substrate, focus or focus error of an optical lithography step, dose or dose error of an optical lithography step, optical aberrations of an optical lithography step, etc. This measurement may be performed on a target of the product substrate itself and/or on a dedicated metrology target provided on a substrate. There are various techniques for making measurements of the structures formed in the patterning process, including the use of a scanning electron microscope, image-based measurement or inspection tools and/or various specialized tools. A relatively fast and non-invasive form of specialized metrology and/or inspection tool is one in which a beam of radiation is directed onto a target on the surface of the substrate and properties of the scattered (diffracted/reflected) beam are measured. By comparing one or more properties of the beam before and after it has been scattered by the substrate, one or more properties of the substrate can be determined. This may be termed diffraction-based metrology or inspection.

Figure 3:
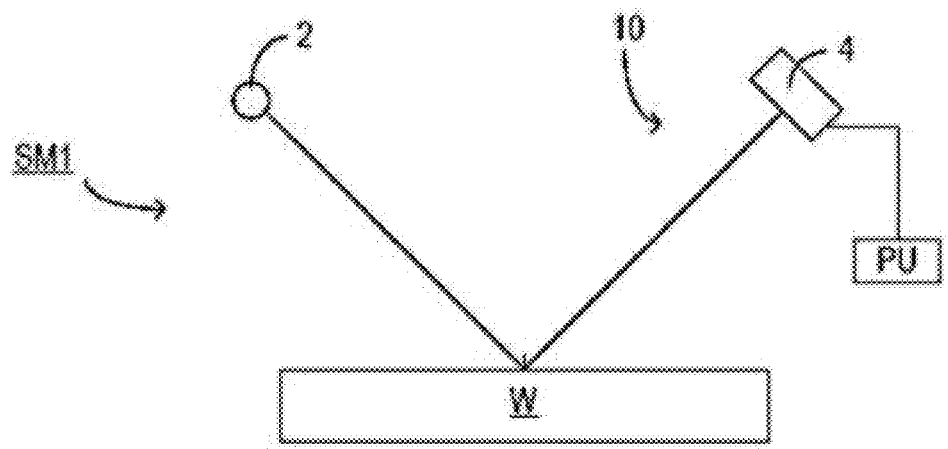
FIG. 3 schematically depicts an example inspection apparatus and metrology technique.
Figure 3:
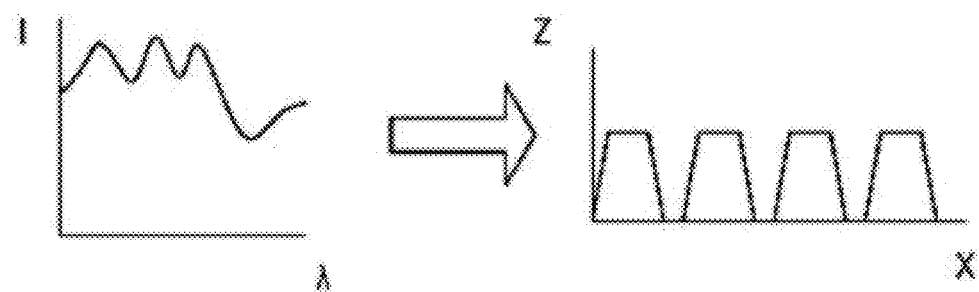

FIG. 3 depicts an example inspection apparatus (e.g., a scatterometer). It comprises a broadband (white light) radiation projector 2 which projects radiation onto a substrate W. The redirected radiation is passed to a spectrometer detector 4, which measures a spectrum 10 (intensity as a function of wavelength) of the specular reflected radiation, as shown, e.g., in the graph in the lower left. From this data, for example, the structure or profile giving rise to the detected spectrum may be reconstructed by processor PU, e.g. by Rigorous Coupled Wave Analysis and non-linear regression or by comparison with a library of simulated spectra as shown at the bottom right of FIG. 3. In general, for the reconstruction the general form of the structure is known and some variables are assumed from knowledge of the process by which the structure was made, leaving only a few variables of the structure to be determined from the measured data. Such an inspection apparatus may be configured as a normal-incidence inspection apparatus or an oblique-incidence inspection apparatus.

Another inspection apparatus that may be used is shown in FIG. 4. In this device, the radiation emitted by radiation source 2 is collimated using lens system 120 and transmitted through interference filter 130 and polarizer 170, reflected by partially reflecting surface 160 and is focused into a spot S on substrate W via an objective lens 150, which has a high numerical aperture (NA), desirably at least 0.9 or at least 0.95. An immersion inspection apparatus (using a relatively high refractive index fluid such as water) may even have a numerical aperture over 1.

As in the lithographic apparatus LA, one or more substrate tables may be provided to hold the substrate W during measurement operations. The substrate tables may be similar or identical in form to the substrate table WT of FIG. 1. In an example where the inspection apparatus is integrated with the lithographic apparatus, they may even be the same substrate table. Coarse and fine positioners may be provided to a second positioner PW configured to accurately position the substrate in relation to a measurement optical system. Various sensors and actuators are provided for example to acquire the position of a target of interest, and to bring it into position under the objective lens 150. Typically many measurements will be made on targets at different locations across the substrate W. The substrate support can be moved in X and Y directions to acquire different targets, and in the Z direction to obtain a desired location of the target relative to the focus of the optical system. It is convenient to think and describe operations as if the objective lens is being brought to different locations relative to the substrate, when, for example, in practice the optical system may remain substantially stationary (typically in the X and Y directions, but perhaps also in the Z direction) and only the substrate moves. Provided the relative position of the substrate and the optical system is correct, it does not matter in principle which one of those is moving in the real world, or if both are moving, or a combination of a part of the optical system is moving (e.g., in the Z and/or tilt direction) with the remainder of the optical system being stationary and the substrate is moving (e.g., in the X and Y directions, but also optionally in the Z and/or tilt direction).

The radiation redirected by the substrate W then passes through partially reflecting surface 160 into a detector 180 in order to have the spectrum detected. The detector 180 may be located at a back-projected focal plane 110 (i.e., at the focal length of the lens system 150) or the plane 110 may be re-imaged with auxiliary optics (not shown) onto the detector 180. The detector may be a two-dimensional detector so that a two-dimensional angular scatter spectrum of a substrate target 30 can be measured. The detector 180 may be, for example, an array of CCD or CMOS sensors, and may use an integration time of, for example, 40 milliseconds per frame.

A reference beam may be used, for example, to measure the intensity of the incident radiation. To do this, when the radiation beam is incident on the partially reflecting surface 160 part of it is transmitted through the partially reflecting surface 160 as a reference beam towards a reference mirror 140. The reference beam is then projected onto a different part of the same detector 180 or alternatively on to a different detector (not shown).

One or more interference filters 130 are available to select a wavelength of interest in the range of, say, 405-790 nm or even lower, such as 200-300 nm. The interference filter may be tunable rather than comprising a set of different filters. A grating could be used instead of an interference filter. An aperture stop or spatial light modulator (not shown) may be provided in the illumination path to control the range of angle of incidence of radiation on the target.

The detector 180 may measure the intensity of redirected radiation at a single wavelength (or narrow wavelength range), the intensity separately at multiple wavelengths or integrated over a wavelength range. Furthermore, the detector may separately measure the intensity of transverse magnetic- and transverse electric-polarized radiation and/or the phase difference between the transverse magnetic- and transverse electric-polarized radiation.

The target 30 on substrate W may be a 1-D grating. In an embodiment, the 1-D grating is printed such that after development, the bars are formed of solid resist lines. The target 30 may be a 2-D grating. In an embodiment, the 2-D grating is printed such that after development, the grating is formed of solid resist pillars or vias in the resist. The bars, pillars or vias may be etched into or on the substrate (e.g., into one or more layers on the substrate).

In an embodiment, the pattern (e.g., of bars, pillars or vias) is sensitive to change in processing in the patterning process (e.g., optical aberration in the lithographic projection apparatus (particularly the projection system PS), focus change, dose change, etc.) and will manifest in a variation in the printed grating. So, in an embodiment, the measured data of the printed grating is used to reconstruct the grating. One or more parameters of the 1-D grating, such as line width and/or shape, or one or more parameters of the 2-D grating, such as pillar or via width or length or shape, may be input to the reconstruction process, performed by processor PU, from knowledge of the printing step and/or other inspection processes.

FIG. 5 illustrates a plan view of a typical target 30, and the extent of illumination spot S in the apparatus of FIG. 4. To obtain a diffraction spectrum that is free of interference from surrounding structures, the target 30, in an embodiment, is a periodic structure (e.g., grating) larger than the width (e.g., diameter) of the illumination spot S. The width of spot S may be smaller than the width and length of the target. The target in other words is 'underfilled' by the illumination, and the diffraction signal Is essentially free from any signals from product features and the like outside the target itself. The illumination arrangement 2, 120, 130, 170 may be configured to provide illumination of a uniform intensity across a back focal plane of objective 150. Alternatively, by, e.g., including an aperture in the illumination path, illumination may be restricted to on axis or off axis directions.

Figure 6:
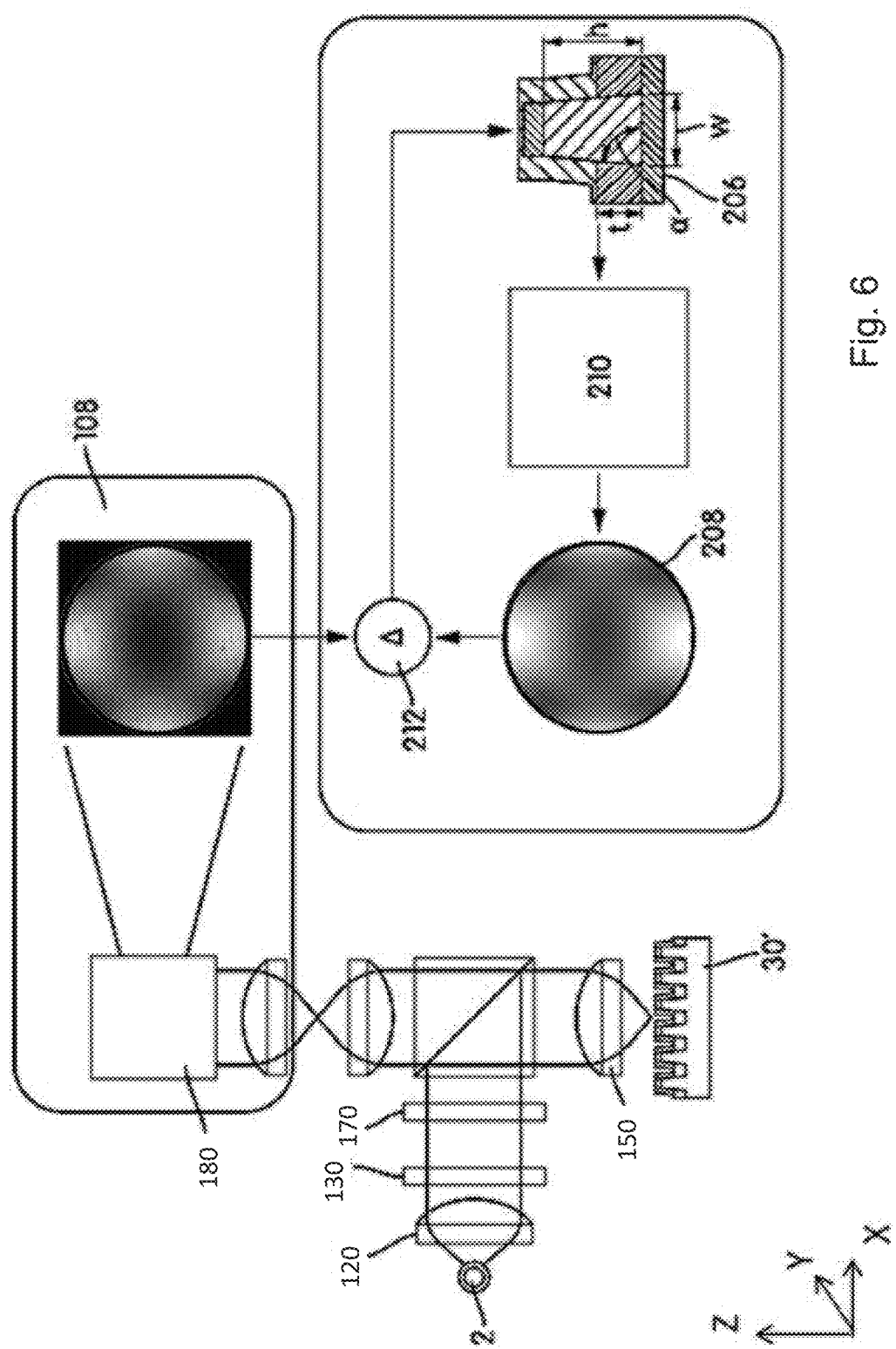
FIG. 6 schematically depicts a process of deriving a plurality of variables of interest based on measurement data.

FIG. 6 schematically depicts an example process of the determination of the value of one or more variables of interest of a target pattern 30' based on measurement data obtained using metrology. Radiation detected by the detector 180 provides a measured radiation distribution 108 for target 30'.

For a given target 30', a radiation distribution 208 can be computed/simulated from a parameterized model 206 using, for example, a numerical Maxwell solver 210. The parameterized model 206 shows example layers of various materials making up, and associated with, the target. The parameterized model 206 may include one or more of variables for the features and layers of the portion of the target under consideration, which may be varied and derived. As shown in FIG. 6, the one or more of the variables may include the thickness t of one or more layers, a width w (e.g., CD) of one or more features, a height h of one or more features, and/or a sidewall angle α of one or more features. Although not shown, the one or more of the variables may further include, but is not limited to, the refractive index (e.g., a real or complex refractive index, refractive index tensor, etc.) of one or more of the layers, the extinction coefficient of one or more layers, the absorption of one or more layers, resist loss during development, a footing of one or more features, and/or line edge roughness of one or more features. The initial values of the variables may be those expected for the target being measured. The measured radiation distribution 108 is then compared at 212 to the computed radiation distribution 208 to determine the difference between the two. If there is a difference, the values of one or more of the variables of the parameterized model 206 may be varied, a new computed radiation distribution 208 calculated and compared against the measured radiation distribution 108 until there is sufficient match between the measured radiation distribution 108 and the computed radiation distribution 208. At that point, the values of the variables of the parameterized model 206 provide a good or best match of the geometry of the actual target 30'. In an embodiment, there is sufficient match when a difference between the measured radiation distribution 108 and the computed radiation distribution 208 is within a tolerance threshold.

In addition to measurement of a parameter by reconstruction, diffraction-based metrology or inspection can be used in the measurement of asymmetry of features in product and/or resist patterns. A particular application of asymmetry measurement is for the measurement of overlay, for example, but other applications are also known. In this case, the target 30 typically comprises one set of periodic features superimposed on another. For example, asymmetry can be measured by comparing opposite parts of the diffraction spectrum from the target 30 (for example, comparing the $-1$st and $+1^{st}$ orders in the diffraction spectrum of a periodic grating). The concepts of asymmetry measurement using the instrument of FIG. 3 or FIG. 4 are described, for example, in U.S. patent application publication US2006-066855, which is incorporated herein in its entirety by reference.

Simply stated, while the positions of the diffraction orders in the diffraction spectrum of the target are determined only by the periodicity of the target, asymmetry in the diffraction spectrum is indicative of asymmetry in the individual features which make up the target. In the instrument of FIG. 4, where detector 180 may be an image sensor, such asymmetry in the diffraction orders appears directly as asymmetry in the pupil image recorded by detector 180. This asymmetry can be measured by digital image processing in unit PU, and calibrated against known values of overlay.

Figure 7A:
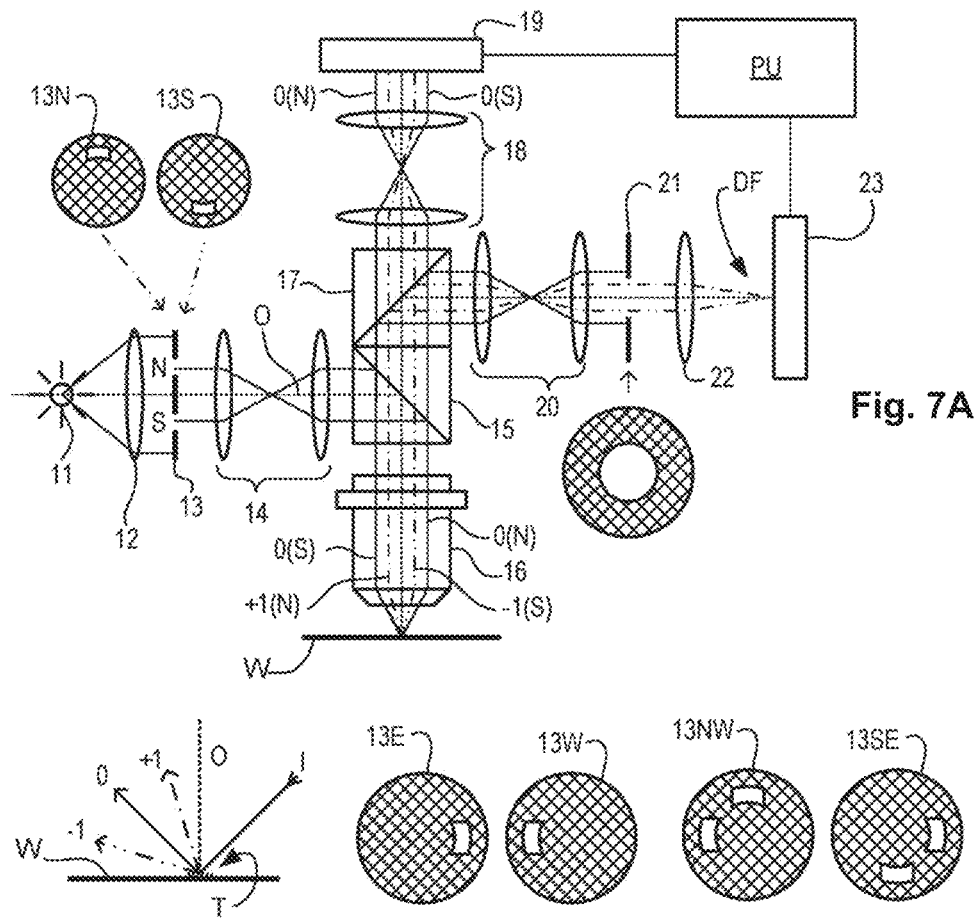
FIG. 7A depicts a schematic diagram of an inspection apparatus configured to measure a target.

A further inspection apparatus suitable for use in embodiments is shown in FIG. 7A. A target T and diffracted rays of measurement radiation used to illuminate the target are illustrated in more detail in FIG. 7B. The inspection apparatus illustrated is of a type known as a dark field metrology apparatus. The inspection apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, radiation emitted by source 11 (e.g., a xenon lamp) is directed onto substrate W via optical element 15 by an optical system comprising lenses 12, 14 and objective lens 16. These lenses are arranged in a double sequence of a 4F arrangement. A different lens arrangement can be used, provided that it, e.g., provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis radiation from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary radiation outside the desired illumination mode will interfere with the desired measurement signals.

Figures 7B, 7C, 7D:
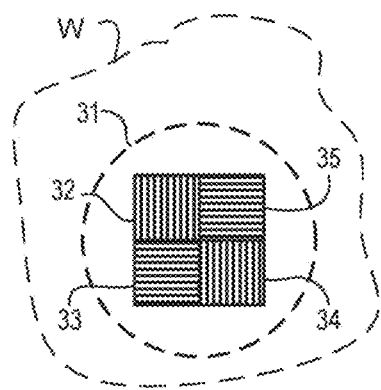
FIG. 7B schematically depicts a detail of a diffraction spectrum of a target periodic structure for a given direction of illumination.
FIG. 7C schematically depicts illumination apertures for providing further illumination modes in using the inspection apparatus of FIG. 7A.
FIG. 7D schematically depicts further illumination apertures for use in the inspection apparatus of FIG. 7A.

As shown in FIG. 7B, target T is placed with substrate W normal to the optical axis O of objective lens 16. The substrate W may be supported by a support (not shown). A ray of measurement radiation I impinging on target T from an angle off the axis O gives rise to a zeroth order ray (solid line 0) and two first order rays (dot-chain line +1 and double dot-chain line −1). It should be remembered that with an overfilled small target, these rays are just one of many parallel rays covering the area of the substrate including metrology target T and other features. Since the aperture in plate 13 has a finite width (necessary to admit a useful quantity of radiation), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the periodic structure pitches of the targets and the illumination angles can be designed or adjusted so that the first order rays entering the objective lens are closely aligned with the central optical axis. The rays illustrated in FIGS. 7A and 7B are shown somewhat off axis, purely to enable them to be more easily distinguished in the diagram.

At least the 0 and +1$^{st}$ orders diffracted by the target T on substrate W are collected by objective lens 16 and directed back through optical element 15. Returning to FIG. 7A, both the first and second illumination modes are illustrated, by designating diametrically opposite apertures labeled as north (N) and south (S). When the incident ray I of measurement radiation is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the inspection apparatus and/or normalizing intensity measurements of the first order beam. The pupil plane image can also be used for many measurement purposes such as reconstruction.

In the second measurement branch, optical system 20, 22 forms an image of the target T on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to processor PU which processes the image, the function of which will depend on the particular type of measurements being performed. Note that the term 'image' is used here in a broad sense. An image of the periodic structure features as such will not be formed, if only one of the −1$^{st}$ and +1$^{st}$ orders is present.

The particular forms of aperture plate 13 and field stop 21 shown in FIGS. 7A, 7C and 7D are purely examples. In an embodiment, on-axis illumination of the targets is used and an aperture stop with an off-axis aperture is used to pass substantially only one first order of diffracted radiation to the sensor. In yet other embodiments, 2nd, 3rd and higher order beams (not shown in FIG. 7A, 7B, 7C or 7D) can be used in measurements, instead of or in addition to the first order beams.

In order to make the measurement radiation adaptable to these different types of measurement, the aperture plate 13 may comprise a number of aperture patterns formed around a disc, which rotates to bring a desired pattern into place. Note that aperture plate 13N or 13S can only be used to measure periodic structures oriented in one direction (X or Y depending on the set-up). For measurement of an orthogonal periodic structure, rotation of the target through 90° and 270° might be implemented. Different aperture plates are shown in FIGS. 7C and 7D. The use of these, and numerous other variations and applications of the apparatus are described in the patent application publications mentioned above.

Figures 8, 9:
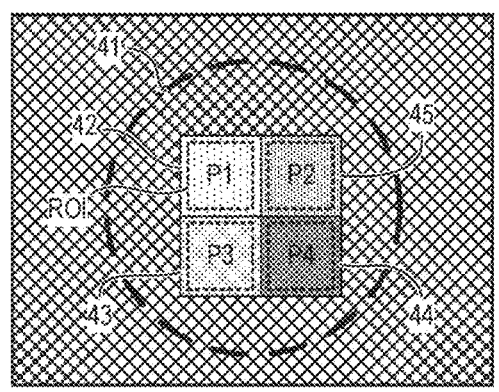
FIG. 8 depicts a form of multiple periodic structure target and an outline of a measurement spot on a substrate.
FIG. 9 depicts an image of the target of FIG. 8 obtained in the inspection apparatus of FIG. 7A.

FIG. 8 depicts a (composite) target formed on a substrate according to known practice. The target in this example comprises four periodic structures (e.g., gratings) 32 to 35 positioned closely together so that they will all be within a measurement spot 31 formed by the metrology radiation illumination beam of the inspection apparatus. The four periodic structures thus are all simultaneously illuminated and simultaneously imaged on sensors 19 and 23. In an example dedicated to measurement of overlay, periodic structures 32 to 35 are themselves composite periodic structures formed by overlying periodic structures that are patterned in different layers of, e.g., the semi-conductor device formed on substrate W. Periodic structures 32 to 35 may have differently biased overlay offsets in order to facilitate measurement of overlay between the layers in which the different parts of the composite periodic structures are formed. Periodic structures 32 to 35 may also differ in their orientation, as shown, so as to diffract incoming radiation in X and Y directions. In one example, periodic structures 32 and 34 are X-direction periodic structures with bias offsets of +d; −d, respectively. Periodic structures 33 and 35 are Y-direction periodic structures with bias offsets +d, −d respectively. Separate images of these periodic structures can be identified in the image captured by sensor 23. This is only one example of a target. A target may comprise more or fewer than 4 periodic structures, or only a single periodic structure.

FIG. 9 shows an example of an image that may be formed on and detected by the sensor 23, using the target of FIG. 8 in the apparatus of FIG. 7, using the aperture plates 13NW or 13SE from FIG. 7D. While the pupil plane image sensor 19 cannot resolve the different individual periodic structures 32 to 35, the image sensor 23 can do so. The dark rectangle represents the field of the image on the sensor, within which the illuminated spot 31 on the substrate is imaged into a corresponding circular area 41. Within this, rectangular areas 42-45 represent the images of the small target periodic structures 32 to 35. If the targets are located in product areas, product features may also be visible in the periphery of this image field. Image processor and control system PU processes these images using pattern recognition to identify the separate images 42 to 45 of periodic structures 32 to 35. In this way, the images do not have to be aligned very precisely at a specific location within the sensor frame, which greatly improves throughput of the measuring apparatus as a whole.

Once the separate images of the periodic structures have been identified, the intensities of those individual images can be measured, e.g., by averaging or summing selected pixel intensity values within the identified areas. Intensities and/or other properties of the images can be compared with one another. These results can be combined to measure different parameters of the patterning process. Overlay performance is an important example of such a parameter.

Figure 10:
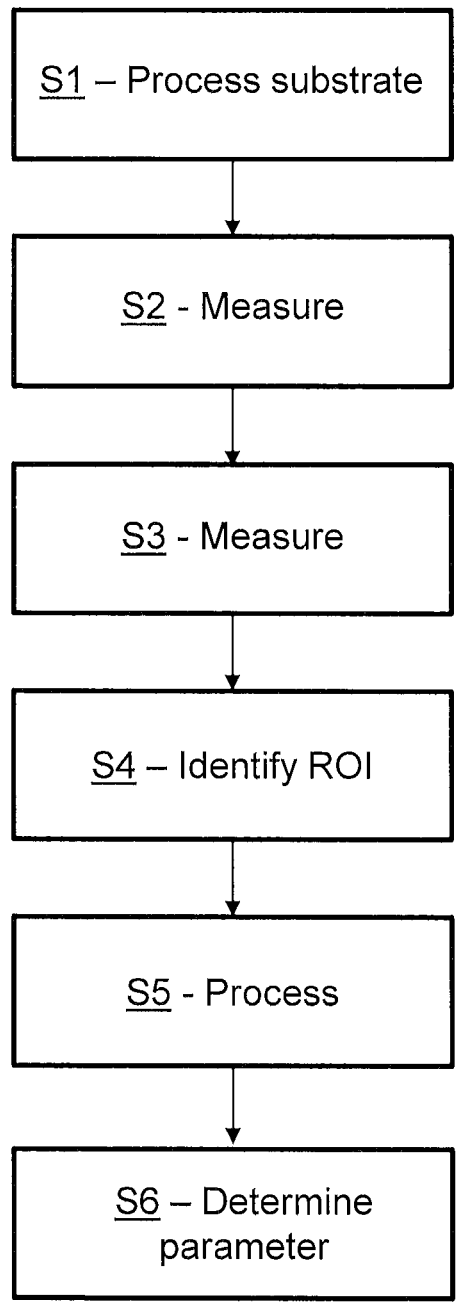
FIG. 10 is a flowchart showing steps of an overlay measurement method using the inspection apparatus of FIG. 3.

FIG. 10 illustrates how, using for example the method described in PCT patent application publication no. WO 2011/012624 (incorporated herein in its entirety by reference), overlay error (i.e., undesired and unintentional overlay misalignment) between the two layers containing the component periodic structures 32 to 35 is measured. This measurement is done through identifying target asymmetry, as revealed by comparing the intensities in the $+1^{st}$ order and $-1^{st}$ order images of the target periodic structures (the intensities of other corresponding higher orders can be compared, e.g. $+2^{nd}$ and $-2^{nd}$ orders) to obtain a measure of the intensity asymmetry. At step S1, the substrate, for example a semiconductor wafer, is processed through a lithographic apparatus, such as the lithographic cell of FIG. 2, one or more times, to create a target including the periodic structures 32-35. At S2, using the inspection apparatus of FIG. 7, an image of the periodic structures 32 to 35 is obtained using only one of the first order diffracted beams (say −1). At step S3, whether by changing the illumination mode, or changing the imaging mode, or by rotating substrate W by 180° in the field of view of the inspection apparatus, a second image of the periodic structures using the other first order diffracted beam (+1) can be obtained. Consequently the +1 diffracted radiation is captured in the second image.

Note that, by including only half of the first order diffracted radiation in each image, the 'images' referred to here are not conventional dark field microscopy images. The individual target features of the target periodic structures will not be resolved. Each target periodic structure will be represented simply by an area of a certain intensity level. In step S4, a region of interest (ROI) is identified within the image of each component target periodic structure, from which intensity levels will be measured.

Having identified the ROI for each individual target periodic structure and measured its intensity, the asymmetry of the target, and hence overlay error, can then be determined. This is done (e.g., by the processor PU) in step S5 comparing the intensity values obtained for $+1^{st}$ and $-1^{st}$ orders for each target periodic structure 32-35 to identify their intensity asymmetry, e.g., any difference in their intensity. The term "difference" is not intended to refer only to subtraction. Differences may be calculated in ratio form. In step S6 the measured intensity asymmetries for a number of target periodic structures are used, together with knowledge of any known imposed overlay biases of those target periodic structures, to calculate one or more performance parameters of the patterning process in the vicinity of the target T.

To enable creation of, e.g., a device structure, a lower periodic structure in an overlay target, etc., an etch apparatus transfers a mask pattern (e.g., a resist pattern) into a hard mask or a functional product layer of a substrate. The result is that the etching by the etch apparatus forms one or more trench type features into the hard mask or the functional product layer of the substrate. In an embodiment, the trench can have various shape or profiles. For example, the trench can be an elongate rectangular type shape (e.g., to form a grating line) or can be a round or rounded shape such as a circle, oval, etc. (e.g., to form a contact hole or to form a grating structure). In an embodiment, the trench can have a rectangular profile but could have a different profile (e.g., a trapezoidal profile).

Control of the shape and profile of the trench (and thus the associated non-trench portions) is becoming more significant as the aspect ratio (i.e., the depth of a trench to its width) increases and the feature sizes (e.g., the width of the trench) get smaller. One etch parameter that should be controlled is tilt in the etching. That is it is desired to control in what tilt direction the etching occurs.

An aspect that affects the tilt in the etching is ion beam tilt. Typically, the ion beam is directed at an angle substantially perpendicular to the major planar surface of the substrate. However, if the trajectory angle of the ions of at least part of the ion beam varies from perpendicular, a slanted etched profile (e.g., a trench tilted from the vertical) can occur. Such ion beam tilt (of all or part of the ion beam) may particularly occur at the substrate edge. Voltage gradients created at the substrate edge due to the change from an electrically biased surface to a grounded or floating surface can occur. These voltage gradients bend the plasma sheath at the substrate edge, which changes the trajectory of ions relative to the substrate. Thus, while the trajectory of ions at a central portion of the substrate can be essentially perpendicular to the surface, the trajectory of ions at the edge of the wafer (e.g., the edge can be considered the outermost 20% or less part of the substrate, the outermost 10% or less part of the substrate, the outermost 5% or less part of the substrate, or the outermost 2% or less part of the substrate, or the outermost 1% or less part of the substrate) can be different than perpendicular, i.e., have an ion beam tilt. In a typical situation of a plasma etching apparatus, the equipotential lines of the plasma sheath would curve upward sharply past an edge of a substrate of a table in the etch apparatus. So, to help solve that, an edge ring is often provided around the substrate to electrically extend the plasma-facing area of the substrate. Thus, the edge ring appears electrically to the plasma to extend some distance outside of the edge of the substrate. Thus, the equipotential lines of the plasma sheath stay relatively constant over the entire surface of the substrate, thereby contributing to process uniformity across the substrate surface. But, in practice, there can still be some curvature of the plasma sheath at the substrate edge, e.g., due to edge ring wear, a difference in potential between the edge ring and the table, etc. The result is a trajectory of plasma ions being at a tilt, leading to an undesired tilt in an etched profile. This may be even more troublesome where a central portion of the substrate has a trajectory of ions substantially perpendicular to the substrate surface. As such, areas of the substrate around the substrate edge would experience a different plasma environment from the plasma environment that exists at the center of substrate, thereby contributing to poor process uniformity across the substrate surface.

So, in an etch apparatus, there are mechanisms that can tune and/or control the trajectory of the ions. For example, the potential between the edge ring and the table can be varied and perhaps spatially around the substrate. There are various, other mechanisms in the art to tune and/or control tilt of the etching (including ion beam tilt) and those are all envisioned by this disclosure.

But, to be able to tune, control and/or correct for the tilt in the etching, there is first of all a desire for a way to know the occurrence of such tilt and optionally the magnitude thereof. So, there is provided herein a metrology technique for being able to detect a structural asymmetry (such as a trench with a slanted wall arising from tilt in etching) in an etched profile of a substrate by measuring the etched profile. In particular, there is provided a monitoring signal that alerts the presence of tilt in the etching through measurement of the etched profile of a substrate. Desirably, the monitoring signal is robust to one or more patterning process variations (e.g., relatively insensitive to etch depth variation). In an embodiment, the monitoring signal of structural asymmetry in the etched profile can alert tilt in the etching without needing to perform a reconstruction as described above of the etched profile, e.g., determining various dimensional parameters of the etched profile using, e.g., a simulator or other mathematical model to compare radiation redirected by the etched profile with simulated or modelled radiation calculated based on expected dimensional parameters.

In an embodiment, the metrology technique for detecting structural asymmetry is an optical technique that involves providing radiation on an etched profile and then, by analysis of the radiation, determining at least a presence of tilt in the etching due to the creation of at least part of the structural asymmetry by the tilt in the etching (e.g., ion beam tilt) on the etched profile. In an embodiment, the signal produced by the metrology technique is relatively insensitive to etch depth variation. That is, in an embodiment, the signal to identify the tilt in the etching will correctly identify the presence (or absence) of tilt in the etching even where there is a relatively small variation in etch depth. In an embodiment, the signal produced by the metrology technique is relatively insensitive to variation in one or more parameters (e.g., wavelength) of the radiation beam. That is, in an embodiment, the signal to identify the tilt in the etching will correctly identify the presence (or absence) of tilt in the etching even where there is relatively small variation in one or more parameters of the radiation beam.

To help understand this metrology technique, FIG. 11A illustrates a highly schematic etched profile 1400 in cross-section from the side. In this example, a trench 1410 has been etched in a hard mask or other layer or part of a substrate. In this case, the trench 1410 forms part of a periodic structure that has a period 1430 with the trench 1410 and its one or more side walls 1420 forming a period. Further, the trench 1410 has a width 1440 (typically corresponding to a CD) and a depth 1450.

In this case, the trench 1410 is at a slant 1460 due to, e.g., an ion beam tilt. The slant 1460 can be represented, for example, by an angle or by a horizontal distance of the top of the wall relative to a bottom of the wall, or vice versa. In an embodiment, the slant herein will be characterized by sidewall angle 1470 (whether in the form of an angle, in the form of a horizontal distance of the top of the wall relative to a bottom of the wall, or in another form). In this example, the sidewall angles at opposite sides of the trench 1410 generally mirror each other (e.g., 88 degrees for one side and 92 degrees at the other); however the sidewall angles at opposite sides do not need to mirror each other (e.g., 88 degrees for one side and 91 degrees (or 88 degrees) for the other side). In an embodiment, the range of sidewall angle due to tilt in the etching ranges from 80 to 89.9 degrees and/or 90.1 to 100 degrees. In an embodiment, the range of sidewall angle due to tilt in the etching ranges from 85 to 89.9 degrees and/or 90.1 to 95 degrees.

FIG. 11B illustrates a highly schematic top view of the etched profile 1400 of FIG. 11A. In this example, the sidewall portion 1425 of one or more sidewalls 1420 is shown with a pattern shading to depict that it slants at an angle although the sidewall portion 1425 in this example is of the same material as the other material surrounding the trench 1410. Further, the trench 1410 is shown as having a rectangular shape when viewed from the top but could have another shape (e.g., circular or oval). As seen in this case, the one or more sidewalls 1480 have a sidewall angle of 90 degrees. But, the one or more sidewalls 1480 could have a non-90 degree sidewall angle if there is tilt in the etching is around the Y direction. The examples here focus just on tilt in the etching around the X direction only but the disclosure herein is applicable to tilt in the etching around any direction.

So, if it weren't for slant 1460, the sidewall angle all around the trench 1410 would be about 90 degrees. And, in that case, the trench 1410 and its one or more sidewalls 1405 would also form a rectangular shape but there would be no sidewall portion 1425 viewable from the top. So, in that case, the trench 1410 would be symmetric since the trench shape has a geometric symmetry when viewed from the top and there is no difference in terms of the nature of the material that makes up the trench 1410.

But, with slant 1460, the trench 1410 now would be asymmetric since the trench profile when viewed from the top has a varying depth at sidewall portion 1425 while at the opposite side of the trench 1410 there is no such varying depth when viewed from the top (the sidewall slant would be below the lip and thus not "seen" by a radiation beam). So, the trench 1410 would be asymmetric anytime the sidewall angle is not symmetric around the trench. That is, the trench has an asymmetric profile.

Figure 12A:
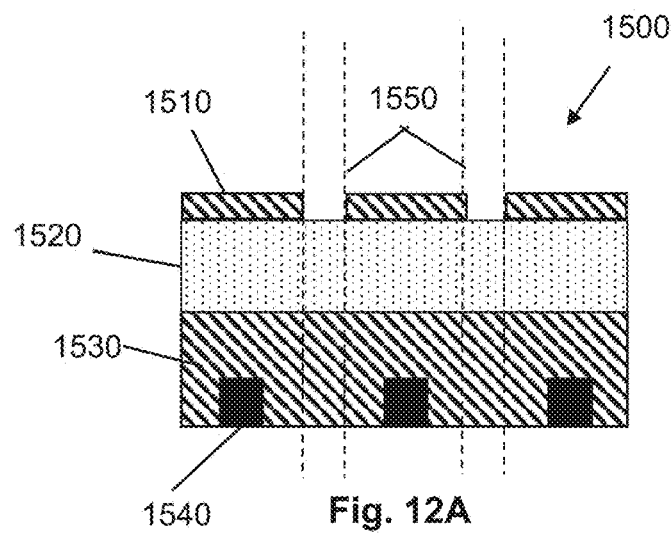
FIG. 12A, FIG. 12B and FIG. 12C highly schematically illustrate how a pattern shift can occur due to a slanted wall of a trench.
Figure 12B:
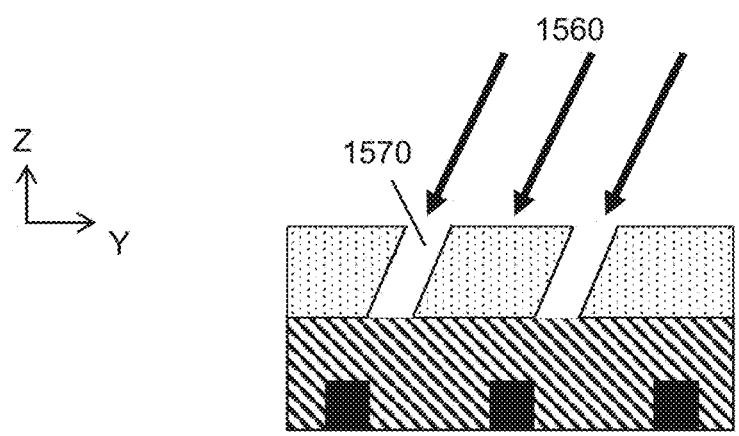
Figure 12C:
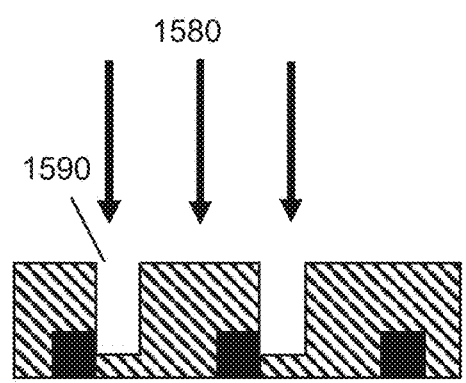

An effect of slant 1460 is highly schematically illustrated in FIGS. 12A-12C. A stack 1500 is shown comprising a resist layer 1510, a hard mask 1520, a product layer 1530, and device features 1540. Further, dashed lines 1550 are depicted to show where the pattern in the resist layer 1510 should be etched. As seen in FIG. 12A and by the dashed lines 1550, an etched pattern should appear in product layer 1530 approximately equal spaced between device features 1540.

However, FIG. 12B shows an example ion beam tilt of the plasma etch 1560 of the hard mask 1520 using the pattern in the resist layer 1510 shown in FIG. 12A. In FIG. 12B, the resist layer 1510 has been removed by the etching (or other process). As seen in FIG. 12B, slanted trenches 1570 are formed in the hard mask 1520 by the etching.

Referring to FIG. 12C, the trenches 1570 in the hard mask 1520 are used to pattern the product layer 1530 using another processing step 1580 (e.g., etching) to form trenches 1590. Even if the processing step 1580 were to yield trenches 1590 with sidewall angles of 90 degrees as shown in FIG. 12C, it can be seen that the trenches have shifted from being equally spaced between device features 1540 as desired by dashed lines 1550 in FIG. 12A. Rather, the trenches 1570 are undesirably unequally spaced between device features 1540. Thus, it can be seen that a slant 1460 can have a significant on proper pattern placement and perhaps on device yield.

So, as discussed above, it is desired to optically determine whether there is tilt in the etching such that appropriate steps can be taken in response thereto such as adjusting the etch apparatus to correct tilt in the etching (e.g., correcting ion beam tilt), making an adjustment in another patterning process step to correct for the effect of the tilt in the etching, signaling rework of the substrate, etc.

As noted above, an optical technique as described herein takes advantage of the asymmetry of the trench 1410 caused by the tilt in the etching. In particular, if radiation is projected onto the trench 1410, a measured pupil using a metrology apparatus such as described above with respect to FIGS. 3-9 shows an asymmetric spatial/angular distribution of radiation within the pupil. This asymmetric spatially/angularly distributed radiation can be used to identify the slant of the sidewall and hence the tilt in the etching.

To take advantage of this technique, the trench with its associated one or more sidewalls has, or is capable of having, a symmetry as discussed above. For example, the trench has reflection symmetry and uniformity in material.

In an embodiment, the trench with its associated one or more sidewalls has asymmetry for a certain feature (such as sidewall angle). Embodiments herein focus on the trench with its associated one or more sidewalls having correct tilt in etching when it is symmetric. However, instead, the trench with its associated one or more sidewalls can have a correct tilt in etching for a certain asymmetry. Appropriate offsets and calculations would then be used to account for the trench with its associated one or more sidewalls having a correct tilt in etching when it has a certain asymmetry. Pertinently, the trench with its associated one or more sidewalls should be capable of change in symmetry (e.g., become asymmetric, or become further asymmetric, or become symmetric from an asymmetric situation) depending on the certain feature value.

Further, in practice, there can be a plurality of trenches arranged periodically to form a target (which target can specially made or be formed of device structures). In an embodiment, the instances of the trench are arranged in a lattice. In an embodiment, the periodic arrangement has a geometric symmetry within the target.

So, in this technique, as discussed further hereafter, advantage is taken of the change in symmetry (e.g., a change to a geometric asymmetry, or change to a further geometric asymmetry, or a change from geometric asymmetry to geometric symmetry) related to a feature of interest (e.g., ion beam tilt) to be able to determine the feature (e.g., ion beam tilt).

A target comprising a physical instance of the trench with its associated one or more sidewalls, such as depicted in FIG. 11, can be illuminated with radiation using, for example, the metrology apparatus of any of FIGS. 3-9. The radiation redirected by the target can be measured, e.g., by a detector. In an embodiment, a pupil of the redirected radiation is measured, i.e., a Fourier transform plane. An example simulated determined such pupil is depicted as the pupil image in FIG. 13A. In this example simulated pupil, only 2 quadrants are shown but as will be appreciated the other quadrants can be measured/simulated. The term pupil and pupil plane herein includes any conjugates thereof unless the context otherwise requires (for example, where a pupil plane of a particular optical system is being identified). The pupil image is effectively an image, specified in terms of an optical characteristic (in this case reflectance) of a pupil of the redirected radiation.

For convenience, the discussion herein will focus on reflectance as an optical characteristic of interest. But, the techniques herein may be used with one or more alternative or additional optical characteristics, such as intensity, polarization and/or phase. Further, for convenience, the discussion herein focuses on detecting and processing images of redirected radiation and in particular pupil images. However, the optical properties of the redirected radiation can be measured and represented in different manners than images. For example, the redirected radiation can be processed in terms of one or more spectrums (e.g., intensity as a function of wavelength). Thus, a detected image of redirected radiation can be considered as an example of an optical representation of the redirected radiation. So, in the case of a pupil plane image, a pupil image is an example of a pupil representation.

Further, the redirected radiation can be polarized. So, in an embodiment, the measurement beam radiation is polarized radiation. In an embodiment, the measurement beam radiation is linearly polarized.

Figure 13A:
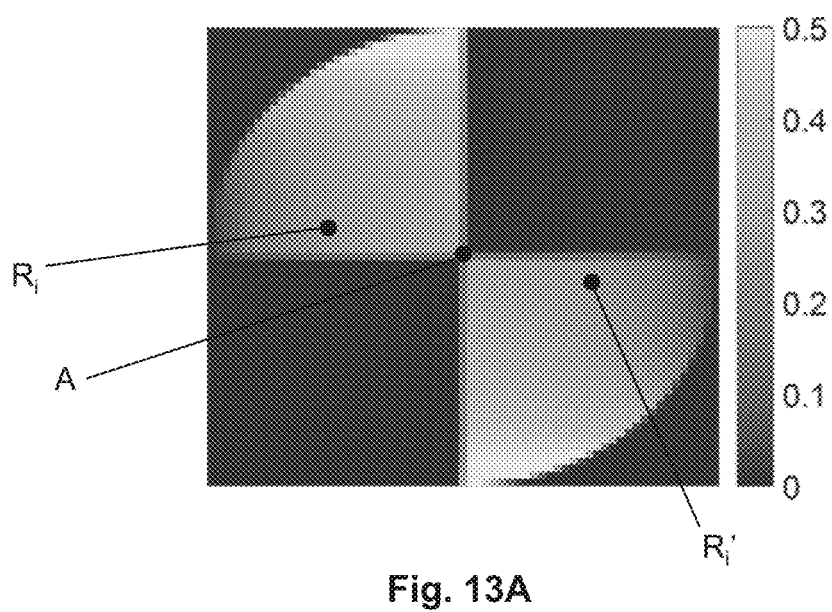
FIG. 13A illustrates a schematic reflectance distribution obtainable by a metrology apparatus.

Having regard to the pupil image of FIG. 13A corresponding to the asymmetric trench with its associated one or more sidewalls, it visually seems like the reflectance distribution is essentially symmetric within the pupil image. However, there is an asymmetric reflectance distribution portion within the pupil image. This asymmetric reflectance distribution portion is due to the asymmetry in the trench with its associated one or more sidewalls. Moreover, the asymmetric reflectance distribution is significantly lower in magnitude than a symmetric reflectance distribution portion in the pupil image.

Figure 13B:
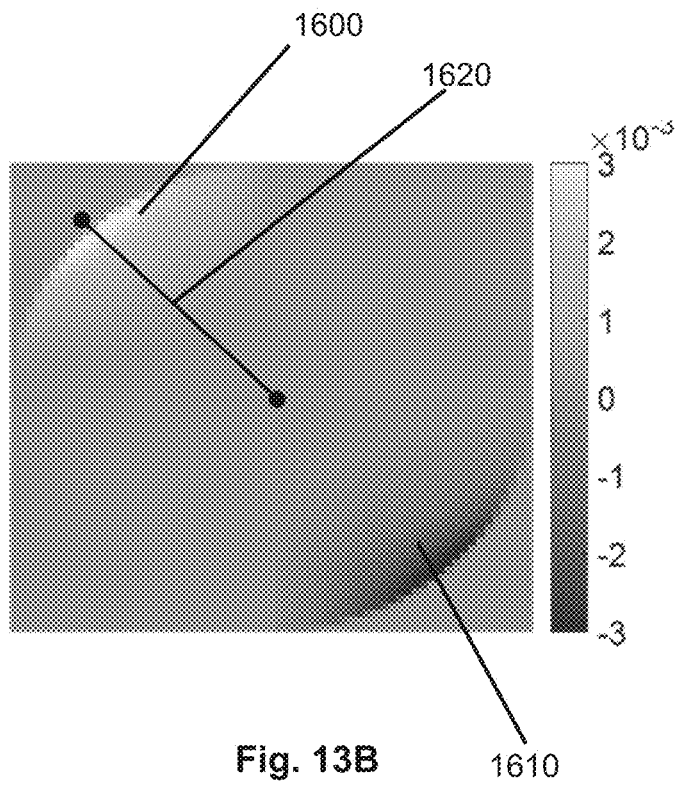
FIG. 13B illustrates a schematic reflectance distribution obtained by differencing two reflectance distributions.

So, in an embodiment, to more effectively isolate the asymmetric reflectance distribution portion, the symmetric reflectance distribution portion can be removed from the pupil image, which results in a derived pupil image of FIG. 13B. To remove the symmetric reflectance distribution portion and obtain the derived pupil image, a particular pupil image pixel (e.g., a pixel) can have the symmetric reflectance distribution portion removed by subtracting from the reflectance at that particular pupil image pixel the reflectance of a symmetrically located pupil image pixel, and vice versa (e.g., located at 180 degrees). In an embodiment, each pixel can correspond to a pixel of the detector, but it need not; for example, a pupil image pixel could be a plurality of the pixels of the detector. Moreover, while reference is made to pixels, it can also be considered in terms of areas (where areas, for example, comprise one pixels or a plurality of pixels). In an embodiment, the point or axis of symmetry across which pixel reflectances are subtracted corresponds with a point or axis of symmetry of the trench with its associated one or more sidewalls. So, for example, considering the pupil image in FIG. 13A, the symmetry reflectance distribution portion can be removed by, for example, subtracting from the reflectance $R_i$ at that particular pixel shown the reflectance $R_i'$ from a symmetrically located pixel, i.e., point symmetrically located with respect to point/axis A. Thus, the reflectance at a particular pixel with the point symmetrical reflectance portion removed, $S_i$, is then $S_i=R_i-R_i'$. This can be repeated for a plurality of pixels of the pupil image, e.g., all the pixels in the pupil image. In an embodiment, the values $S_i$ can be normalized values. That is, they can be divided by a reflectance value. For example, they can be normalized by (i.e., divided by) the average reflectance for the areas/points under consideration (e.g., (abs($R_i$)+abs($R_i'$))/2).

As seen in the derived pupil image of FIG. 13B, the reflectance distribution, obtained using a physical instance of an asymmetric trench with its associated one or more sidewalls, is not symmetric. As seen in regions 1600 and 1610, there is an asymmetric reflectance distribution portion visible once the symmetric reflectance distribution portion is removed (herein referred to asymmetric reflectance and which can be normalized as discussed herein). As seen from the scale, in an embodiment, the magnitude of the asymmetric reflectance is small compared to the reflectance in general (see, e.g., approximately 0.3 average reflectance for FIG. 13A but a highest reflectance of about 0.003 for FIG. 13B). Thus, the asymmetric reflectance can present a weak signal.

Figure 13C:
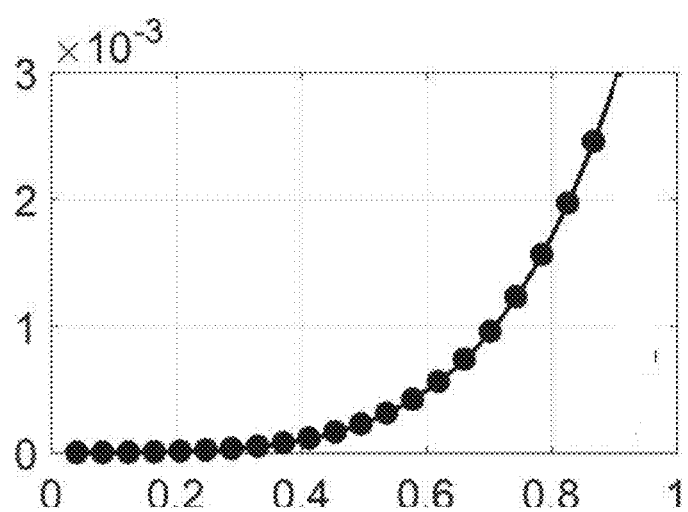
FIG. 13C illustrates a graph of reflectance against numerical aperture of the pupil.

Further, FIG. 13C shows the asymmetric reflectance values along the diagonal 1620 in FIG. 13B. In the graph of FIG. 13C, the vertical axis corresponds to the asymmetric reflectance value and the horizontal axis corresponds to the numerical aperture and thus the position along the diagonal, where 0 corresponds to the center of the pupil of FIG. 13B and 1 corresponds to the outer boundary of the pupil. It can be seen from FIG. 13C that, in an embodiment, the asymmetric reflectance only effectively becomes observable at large angles of incidence (NA) (and even then can be relatively weak).

But, despite the possibility of the asymmetric reflectance being relatively weak and/or effectively only observable at relatively high angles of incidence, an asymmetry in the geometrical domain can correspond to an asymmetry in the pupil. So, in an embodiment, a method is provided that uses the optical response of one or more trenches (with associated one or more sidewalls) that possesses, or is capable of, inherent symmetry to determine a parameter (e.g., ion beam tilt) corresponding to a physical configuration change that causes a change in symmetry (e.g., causes an asymmetry, or causes a further asymmetry, or causes an asymmetric arrangement to become symmetric) of the physical instance of the one or more trenches (with associated one or more sidewalls). In particular, in an embodiment, an etching tilt induced asymmetry (or lack thereof) in the pupil as measured by a metrology apparatus can be exploited to determine the presence of the etching tilt. That is, the pupil asymmetry is used to determine the occurrence of the effect of a tilt in the etching within the physical instance of the one or more trenches (with associated one or more sidewalls) within the target.

Figure 14:
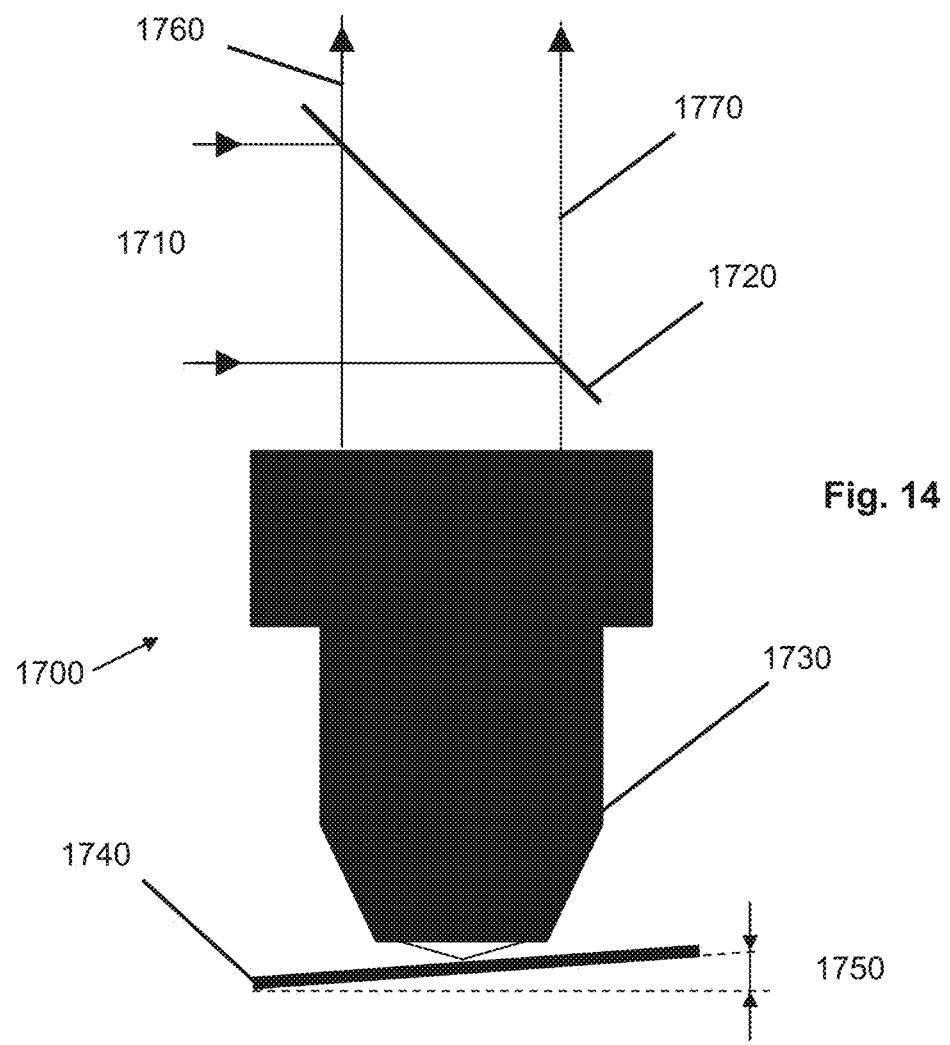
FIG. 14 is a highly schematic representation of the objective of a metrology apparatus in association with a substrate.

Now, with the possibility of the asymmetric reflectance being relatively weak and/or effectively only observable at relatively high angles of incidence, a relatively small tilt of the substrate in of itself can also introduce an asymmetry in the redirected radiation. This asymmetry arising from substrate tilt is schematically depicted in FIG. 14. FIG. 14 is a highly schematic representation of an optical objective of a metrology apparatus 1700 in association with a substrate.

An objective 1730 of the metrology apparatus is shown in conjunction with a substrate 1740. As seen in this example, the substrate 1740 is at a tilt 1750. So, when the tilted substrate 1740 is illuminated by illumination 1710 (that is in this example directed into the objective 1730 by a partially reflective mirror 1720), the radiation, after passing through the objective 1730 and redirected by the substrate 1740, passes back through the objective 1730 (and in this example, partially reflective mirror 1720) to provide radiation 1760 to a detector (not shown for convenience) at a first side of the pupil and radiation 1770 at a second side of the pupil opposite the first side across a center of the pupil.

In this situation, it has been determined that the asymmetry in the reflectance between radiation 1760 and 1770 (and which difference is further normalized to the reflectance of the substrate at zero tilt) can be described by the following formula:

$$\frac{R_l - R_r}{R_0} = 2\theta \frac{NA}{\sqrt{1-NA^2}} \qquad (6)$$

wherein $\theta$ corresponds to the tilt of the substrate at the location of incidence of the radiation (e.g., tilt 1750), $R_l$ corresponds to the reflectance at the first side of the pupil (e.g., the reflectance for radiation 1760), $R_r$ corresponds to the reflectance at the second side of the pupil opposite a center of the pupil to the first side (e.g., the reflectance for radiation 1760), $R_0$ corresponds to the reflectance when $\theta=0$ (e.g., a tilt 1750 of zero), and NA corresponds to the numerical aperture of the objective.

Figure 15:
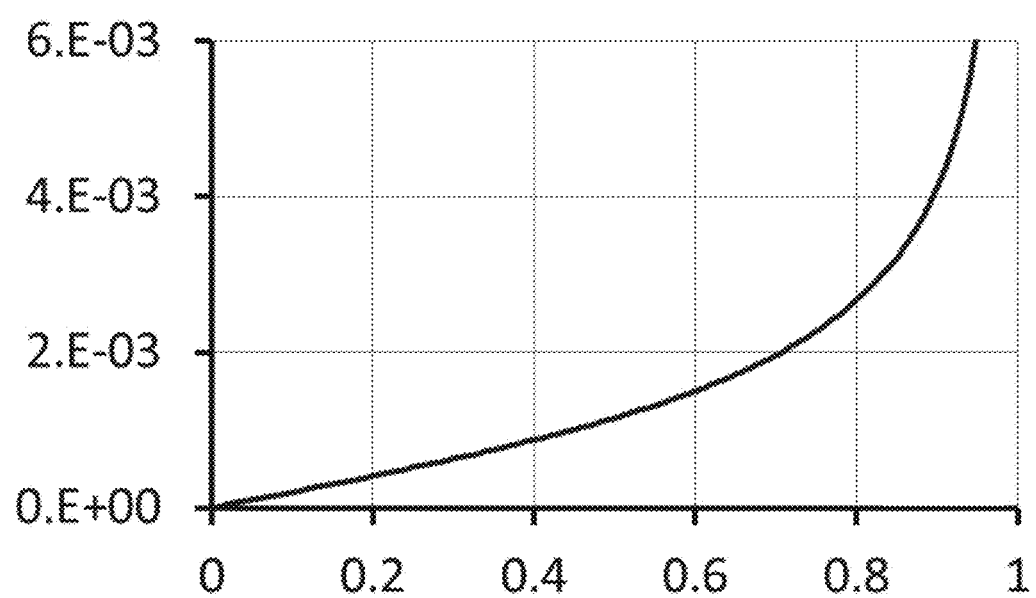
FIG. 15 is an example graph of relative asymmetry of reflectance of radiation from a substrate at a certain tilt angle of the substrate.

FIG. 15 is an example graph of relative asymmetry in the reflectance of radiation from a substrate at a certain tilt angle of the substrate. The vertical axis is the normalized asymmetry in the reflectance at the first and second sides of the pupil, e.g., $$\frac{R_l - R_r}{R_0}$$

and the horizontal axis is the numerical aperture. In this case, the relative asymmetry values are determined for a substrate tilt of 1 mrad at the incidence location. As seen in the graph, the effect of the relative asymmetry of reflectance for even a small substrate tilt increases significantly with increasing numerical aperture (just like the asymmetry in reflectance due to structural asymmetry in the etched profile as discussed above). Moreover, the magnitude of the asymmetry in the reflectance due to substrate tilt can be comparable, if not greater, than the asymmetry in reflectance due to structural asymmetry in the etched profile as discussed above. So, a challenge is that the substrate tilt also creates asymmetry in the pupil, although it has been determined that this asymmetry does not depend on wavelength. Thus, it is desired to separate the asymmetry in reflectance due to structural asymmetry in the etched profile from the asymmetry in the reflectance due to substrate tilt. Rotating the substrate 180° is not an option since both the asymmetry in the reflectance due to substrate tilt and the asymmetry in reflectance due to structural asymmetry in the etched profile will both rotate with the substrate rotation.

Furthermore, if an example 0.1° metrology precision is desired, this corresponds to a measured asymmetry in reflectance of approximately:

$$\frac{0.1°}{2°} \times 0.01 = 5 \times 10^{-4} \quad (10)$$

wherein 2° is an example approximation of the sidewall angle variation from perpendicular. However, having regarding to FIG. 15, 1 mrad of substrate tilt already gives an asymmetric reflectance value of around $4 \times 10^{-3}$ at a NA of about 0.9. So, one option in this example case is to control the local substrate tilt to within about 100 μrad such that the measured asymmetry can be in the range of $5 \times 10^{-4}$ to obtain a desired 0.1° metrology precision. However, this can be very challenging at the edge of a substrate.

So, in an embodiment, to separate the asymmetry in reflectance due to structural asymmetry in the etched profile from the asymmetry in the reflectance due to substrate tilt, the etched profile of interest is measured at two different wavelengths under the same substrate tilt conditions (e.g., there is no relative movement between the substrate and the measurement illumination beam path between the illumination at the different wavelengths) to obtain gross asymmetric reflectance values (e.g., normalized asymmetric reflectance values) at each wavelength. Then, a difference is found between the gross asymmetric reflectance values which effectively eliminates the contribution of the substrate tilt to those values. That is, the asymmetry in reflectance due to substrate tilt is removed. This is because the same amount of contribution to the asymmetric reflectance values due to substrate tilt is common to both gross asymmetric reflectance values since the contribution to the asymmetric reflectance values due to substrate tilt is independent of wavelength. The result is the asymmetric reflectance value due to structural asymmetry in the etched profile. If that asymmetric reflectance value due to structural asymmetry in the etched profile is non-zero, then there is likely a structural asymmetry in the etched profile and thus represents a potential tilt in the etching (e.g., an ion beam tilt). In an embodiment, the technique can detect a tilt in the etching in the range from 80 to 89.9 degrees and/or 90.1 to 100 degrees (wherein 90 degrees is perpendicular to a main surface of the substrate). In an embodiment, the technique can detect a tilt in the etching within 5 degrees from perpendicular, e.g., in the range from 85 to 89.9 degrees and/or 90.1 to 95 degrees.

Figure 16:
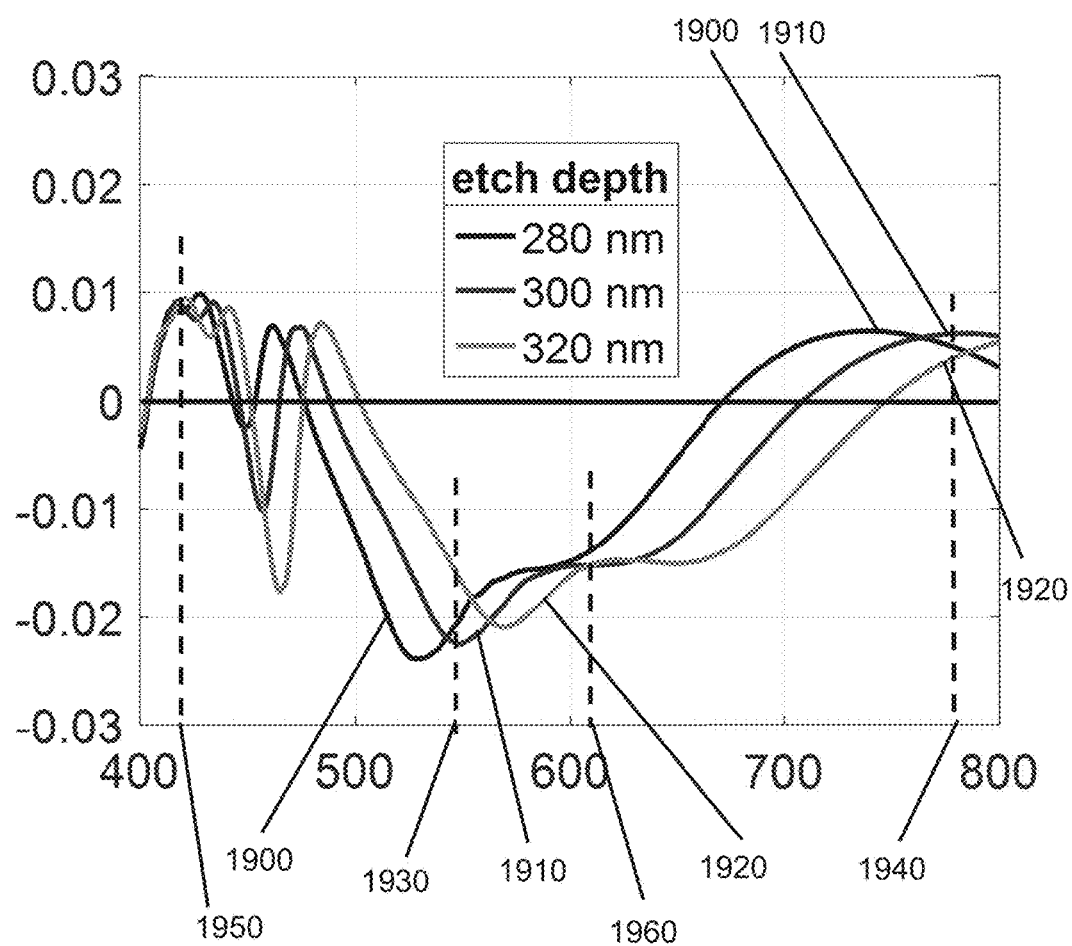
FIG. 16 is example graph of relative asymmetry of reflectance of radiation from a substrate with an etched profile.

So, to enable this process, at least two different wavelengths should be identified at which the etched profile of interest should be measured. FIG. 16 is an example graph of asymmetric reflectance values from a substrate with an etched profile. The horizontal axis corresponds to wavelength of the measurement radiation. The vertical axis is the asymmetric reflectance (i.e., the difference between a value of the reflectance for a pupil location and a value of the reflectance for another pupil location that is point symmetrically positioned with respect to a point at a central portion of the pupil). In the case of FIG. 16, the asymmetric reflectance is normalized by, in this case, the average (e.g., mean) reflectance. So, the vertical axis can be represented as:

$$\frac{R_0 - R_{180}}{R_M} \quad (11)$$

wherein $R_0$ is the value of the reflectance for a first pupil location (e.g., a pixel, a plurality of pixels, an area, etc.), $R_{180}$ is the value of the reflectance for a second pupil location (e.g., a corresponding pixel, plurality of pixels, area, etc.), which second pupil location is point symmetrically positioned with respect to a point at a central portion of the pupil, and $R_M$ is the average (e.g., mean) value of the reflectance for the first and second pupil locations (e.g., abs($R_0$)+abs($R_{180}$))/2).

Further, data is shown in FIG. 16 for each of three different etch depths of the etched profile. In this example, data is provided for 280 nm, 300 nm and 320 nm etch depths. Specifically, line 1900 corresponds to the 280 nm etch depth, line 1910 corresponds to the 300 nm etch depth and the line 1920 corresponds to the 320 nm etch depth.

In the example of FIG. 16, the data was generated by a simulator. In addition or alternatively, the data can be generated by experiment by illuminating etched profiles of interest with different etch depths, each at a plurality of different wavelengths. Furthermore, while the data has been graphed as shown in FIG. 16, it need not be so graphed. Any analysis can be performed on the underlying data without having to generate curves as shown in FIG. 16.

As seen in FIG. 16, the pupil asymmetry due to trench structural asymmetry shows a swing curve. That is, in an embodiment, the pupil asymmetry varies with wavelength. The swing curve shows why a difference between gross asymmetric reflectance values at different wavelengths is effective to remove the asymmetric reflectance value due to substrate tilt yet retain an asymmetric reflectance value due to structural asymmetry in the etched profile provided appropriate wavelengths are chosen.

In an embodiment, the two different wavelengths chosen are those on opposite sides of the swing curve, i.e., a first wavelength at which the asymmetric reflectance has a positive value and a second wavelength at which the asymmetric reflectance has a negative value. In an embodiment, the two different wavelengths are chosen at maximum and minimum peaks along a swing curve or at a value within 20%, within 10% or within 5% of maximum and minimum peak values from the respective maximum and minimum peak values (e.g., 80%-100% of the maximum and/or minimum peak value, 90-100% of the maximum and/or minimum peak value or 95-100% of the maximum and/or minimum peak value). In an embodiment, the first and second wavelengths are chosen that satisfy any of the foregoing criteria for each of the different etch depths. For example, the wavelength 1940 (e.g., about 780 nm) is a good candidate where each of the curves 1900, 1910 and 1920 is near a maximum peak. Similarly, the wavelength 1930 (e.g., about 550 nm) is another good candidate where each of the curves 1900, 1910 and 1920 is near a minimum peak. As another example, the wavelength 1950 (e.g., about 415 nm) is a good candidate where each of the curves 1900, 1910 and 1920 is near a maximum peak. And, the wavelength 1960 (e.g., about 605 nm) is another good candidate where each of the curves

1900, 1910 and 1920 is fairly near a minimum peak (but has an advantage, as described hereafter, of the values of each of the curves 1900, 1910 and 1920 being about the same).

In an embodiment, the two different wavelengths are chosen such that the respective values of asymmetric reflectance at the wavelength are relatively insensitive to variation in depth of etching of the etched profile. In other words, desirably, the two different wavelengths have respective values of asymmetric reflectance that are the same or close the same for each of a plurality of depths of etching. In this manner, the etch depth variation of the etched profile can vary as part of the etch process but still yield measured values at the different wavelengths that will signal a tilt in the etching. In an embodiment, relatively insensitive means that a change of less or equal to ±20%, ±10% or ±5% of the depth of etching yields a change of less than or equal to ±20%, ±10% or ±5% of the value of asymmetric reflectance. For example, each of wavelengths 1930, 1940, 1950 and 1960 are good candidates of where each of the curves 1900, 1910 and 1920 representing different etch depths yields a substantially same, or similar, value of asymmetric reflectance.

In an embodiment, the two different wavelengths are chosen such that the respective values of asymmetric reflectance at the wavelength are relatively insensitive to variation in the wavelength of the measurement radiation beam. In other words, desirably, the two different wavelengths have respective values of asymmetric reflectance that are the same or close the same for each of a plurality of wavelengths near to the respective wavelengths. In an embodiment, relatively insensitive means that a change of less or equal to ±15%, ±10% or ±5% of a particular wavelength yields a change of less than or equal to ±15%, ±10% or ±5% of the value of asymmetric reflectance. For example, each of wavelengths 1930, 1940, 1950 and 1960 are good candidates of where each of the curves 1900, 1910 and 1920 has a relatively low slope such that, despite a variation in wavelength, a substantially same or similar value of asymmetric reflectance would be measured.

So, by selecting wavelengths at opposite sides of the swing curve and/or wavelengths at which the values of asymmetric reflectance are relatively insensitive, the metrology can robustly (e.g., to process variation such as etch depth variation) detect the presence of asymmetry in patterns at, e.g., a device pitch (such as pitches at or below 100 nm).

In an embodiment, the etched profile has a pitch of about 100 nm or less. Those pitches are representative of functional device structure pitches and so the etched profile can be representative of etching of device structures. In an embodiment, the etched profile with a pitch of about 100 nm or less is measured with radiation having a wavelength of 400 nm or more.

In an embodiment, at a pitch of 100 nm or less with measurement radiation with a wavelength of 400 nm or more, the redirected radiation is substantially only 0th diffraction order radiation, wherein the asymmetry signal is relatively weak and generally only visible for large angles of incidence as described above. So, in an embodiment, a pupil representation is of primarily, or substantially, one diffraction order of redirected radiation from the target. For example, the radiation can be 80% or more, 85% or more, 90% or more, 95% or more, 98% or more or 99% or more, of a particular order of the radiation. In an embodiment, the pupil representation is of primarily, or substantially, zeroth order redirected radiation. This can occur, for example, when the pitch of the target, the wavelength of the measurement radiation, and optionally one or more other conditions cause the target to redirect primarily zeroth order (although there can be radiation of one or more higher orders). In an embodiment, a majority of the pupil representation is zeroth order redirected radiation. However, in an embodiment, the pupil representation does not need to comprise substantially only $0^{th}$ order radiation.

In an embodiment, the beam spot of the measurement illumination beam is filled with the trench or a plurality of trenches, that has the structural asymmetry so that the measured pupil asymmetry corresponds substantially only to the structural asymmetry caused by the tilt in etching. If there are other structures in the beam spot that have structural asymmetry not caused the tilt in etching, those should be blocked or otherwise removed from the analysis. In an embodiment, the beam spot can illuminate, besides the trench or plurality of trenches that has the structural asymmetry, flat surfaces or symmetrical structures since those should not contribute to asymmetry in reflectance.

Figure 17:
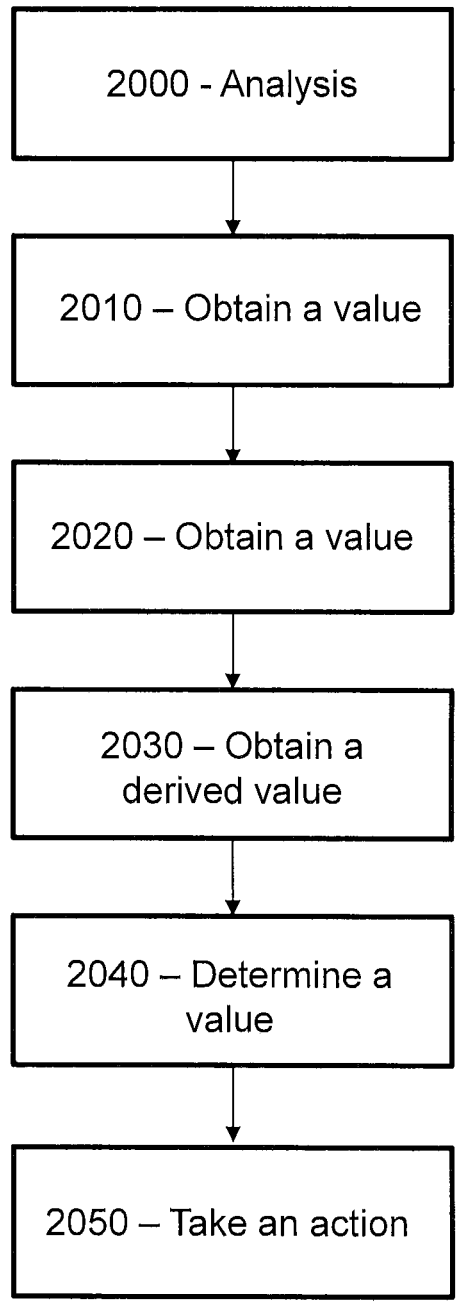
FIG. 17 is a flowchart of steps of a method according to an embodiment.

FIG. 17 is a flowchart of steps of a method according to an embodiment. Not all of the steps of this method are required to be performed together. Further, one or more steps may be optional (e.g., step 2000 is not necessary if two different wavelengths are otherwise known).

At 2000, an analysis if performed to find at least two different wavelengths for which an optical characteristic of an etched profile can be measured so as to determine the occurrence of a tilt in the etching used to create the etched profile. In an embodiment, the analysis may be that described above with respect to FIG. 16.

At 2010, a first value of an optical characteristic (e.g., reflectance) determined for the etched profile measured at a first of the at least two wavelengths of measurement radiation is obtained. This can involve measuring the etched profile of interest with measurement radiation at the first wavelength to determine a first optical characteristic value. In an embodiment, the first optical characteristic value is an asymmetric optical characteristic value (i.e., the difference between a value of the optical characteristic for a pupil location and a value of the optical characteristic for another pupil location that is point symmetrically positioned with respect to a point at a central portion of the pupil). In an embodiment, the first optical characteristic value is a normalized value. This measurement can use an apparatus such as described with respect to FIGS. 3-9.

At 2020, a second value of the optical characteristic (e.g., reflectance) determined for the etched profile measured at a second of the at least two wavelengths of measurement radiation is obtained. This can involve measuring the etched profile of interest with measurement radiation at the second wavelength to determine a second optical characteristic value. In an embodiment, the second optical characteristic value is an asymmetric optical characteristic value (i.e., the difference between a value of the optical characteristic for a pupil location and a value of the optical characteristic for another pupil location that is point symmetrically positioned with respect to a point at a central portion of the pupil). In an embodiment, the second optical characteristic value is a normalized value. This measurement can use an apparatus such as described with respect to FIGS. 3-9.

At 2030, a derived value that represents a difference between the first and second optical characteristic values is obtained. For example, the derived value can be the difference between asymmetric optical characteristic values determined with measurements taken with an illumination beam at each of the first and second wavelengths. In an embodiment, the derived value is a normalized value (e.g., when the first and second optical characteristic values are respective normalized values).

At 2040, based on the first and second optical characteristic values or on the derived value, an occurrence of a tilt in the etching to form the etched profile is determined. In an embodiment, an occurrence of tilt in the etching can be determined when the derived value is non-zero or exceed a certain threshold amount (e.g., to account for error). In an embodiment, an occurrence of tilt in the etching can be determined when the first and second optical characteristic values are not equal or a difference between them exceeds a certain threshold amount (e.g., to account for error).

At 2050, responsive to determining occurrence of tilt in the etching, one or more actions can be taken.

One example action is to initiate an error with respect to the substrate. For example, the error signal can indicate that the substrate should not be further processed, should be reworked, should be discarded, etc. The error signal can be automatically processed to instigate its associated process (e.g., rework, discard, etc.).

Another example action is to make an adjustment in a patterning process step to correct for the effect of the tilt in the etching. For example, a feedback (or feedforward) correction can be made to a part of the patterning process (e.g., a correction in a lithography step) used to create the etched profile or of another patterning process. For example, an alignment or optical correction could be made to account for pattern shift associated with the identified tilt in the etching. As another example, the design of a part of a patterning process can be changed (e.g., change in the material, thickness, etc. of the etch mask, change in the patterning device pattern, etc.).

Another example action is to adjust the etch apparatus to correct for tilt in the etching (e.g., correcting ion beam tilt). For example, the occurrence of the tilt in the etching might identify a defect in the etch apparatus that requires, for example, repair or replacement of all or part of the etch apparatus, a need for maintenance of the etch apparatus, etc. Following such repair, replacement, or maintenance, the tilt in the etching may be corrected.

As another example of adjusting the etch apparatus to correct for tilt in the etching, a tuning or control feature of the etch apparatus can be used to tune or control the amount of tilt in the etching (desirably correcting or controlling the tilt to a desired tilt such as essentially perpendicular to the substrate). So, in an embodiment, the tuning or control of the tilt in etching can be based on the results of the analysis at step 2040. To facilitate such tuning or control, the nature (e.g., angle) of the tilt in the etching should be determined. A value of the tilt in the etching (e.g., ion beam tilt angle) can be done one or more various ways.

As a basic example of determining the nature of the tilt, the etched profile can be examined with, e.g., a scanning electron microscope. In an embodiment, the etched profile can be sliced and imaged to determine the sidewall angle tilt.

As another example of determining the nature of the tilt, a reconstruction as described above can performed to derive the one or more sidewall angles and the ion beam tilt that would produce such one or more sidewall angles. This can be computationally more efficient as a reconstruction could only, or mostly only, be performed where a tilt in the etching has already been identified.

As another example of determining the nature of the tilt, a "set-get" calibration method can be performed in which the techniques described herein are used with a tilt in the etching that is set to various particular angles to obtain respective etched profiles and then those etched profiles are measured to get values of asymmetric reflectance for those set angles. Then, when a subsequent etched profile is measured to obtain an asymmetric reflectance value that signals a tilt in the etching, that asymmetric reflectance value can be compared to the calibration asymmetric reflectance values to determine an associated tilt angle in the etching. Where an exact match is not available, interpolation or extrapolation can be used to arrive at an estimated ion beam tilt angle.

So, with the techniques described herein, it is possible to identify a tilt in the etching without having to perform, e.g., complicated and complex reconstruction or destructive and/or time consuming imaging. Moreover, in an embodiment, the techniques described herein can avoid highly precise tilt control during measurement because it can account for substrate tilt.

While much of the discussion has focused on target structures as metrology targets specifically designed and formed for the purposes of measurement, in other embodiments, the tilt in etching may be determined using targets which are functional parts of devices formed on the substrate. Many devices have regular, periodic structures akin to a grating. The term "target", "grating" or "periodic structure" of a target as used herein does not require that the applicable structure has been provided specifically for the measurement being performed. Further, pitch P of the metrology target is close to the resolution limit of the optical system of the measurement tool, but may be larger than the dimension of typical product features made by a patterning process in the target portions C. In practice the features and/or spaces of the periodic structures may be made to include smaller structures similar in dimension to the product features.

Further, while the discussion has focused on, e.g., individual pixel values of an optical characteristic, it will be appreciated that the techniques herein can be based on collections of pixel values or values for areas. Further, the techniques herein can be based on statistical measures (e.g., a mathematical average) of the optical characteristic. As an example, the calculations and comparisons can be based on a mathematical average for a certain region of the pupil (e.g., a quadrant), which can then be normalized (e.g., by an average of the averages for two different areas).

In an embodiment, there is provided a method comprising: obtaining a first value of an optical characteristic determined for an etched profile of a substrate measured at a first wavelength of measurement radiation, obtaining a second value of the optical characteristic determined for the etched profile of the substrate measured at a second wavelength of measurement radiation, and obtaining a derived value that represents a difference between the first and second values; and determining, by a hardware computer and based on the first and second values or on the derived value, an occurrence of a tilt in the etching to form the etched profile.

In an embodiment, the first and second values are obtained for an etched profile having a structural asymmetry caused due to the tilt in the etching. In an embodiment, the determining is based on the derived value. In an embodiment, the first and second wavelengths are such that the first and second values are relatively insensitive to variation in depth of etching of the etched profile. In an embodiment, relatively insensitive means that a change of less or equal to ±20% of the depth of etching yields a change of less than or equal to ±20% of the first and second values. In an embodiment, the optical characteristic is reflectance. In an embodiment, the optical characteristic values comprise asymmetric optical characteristic values obtained by subtracting a value of the optical characteristic for a pupil location from a value of the optical characteristic for a pupil location that is point symmetrically positioned with respect to a point at a central portion of the pupil. In an embodiment, the first value is a negative value and the second value is positive value, or vice versa. In an embodiment, the optical characteristic values are normalized values. In an embodiment, the tilt in the etching comprises ion beam tilt. In an embodiment, the etched profile has a pitch of about 100 nm or less. In an embodiment, the first and second wavelengths are selected from the range of 400 nm to 800 nm. In an embodiment, the occurrence of tilt in the etching comprises an occurrence a tilt within 5 degrees of perpendicular of a main surface of the substrate.

In an embodiment, there is provided a method, comprising: obtaining asymmetric optical characteristic values for an asymmetric etched profile of a substrate at each of a plurality of different wavelengths of measurement radiation, wherein the asymmetry of the etched profile is caused by tilt in the etching and each of the asymmetric optical characteristic values corresponds to a difference between a value of the optical characteristic for a first pupil location and a value of the optical characteristic for a second pupil location that is point symmetrically positioned with respect to a point at a central portion of the pupil; and identifying, by a hardware computer and based on the values, a first wavelength of measurement radiation at which a first value of the asymmetric optical characteristic values is negative and a second wavelength of measurement radiation at which a second value of the asymmetric optical characteristic values is positive, wherein occurrence of tilt in the etching of another etched profile can be determined by finding a difference between a value of the asymmetric optical characteristic determined for the other etched profile using a measurement at the first wavelength and a value of the asymmetric optical characteristic determined for the other etched profile using a measurement at the second wavelength.

In an embodiment, the first and second wavelengths are such that the first and second values are relatively insensitive to variation in depth of etching of the etched profile. In an embodiment, relatively insensitive means that a change of less or equal to ±20% of the depth of etching yields a change of less than or equal to ±20% of the first and second values. In an embodiment, the optical characteristic is reflectance. In an embodiment, the tilt in the etching comprises ion beam tilt. In an embodiment, the first and second wavelengths are selected from the range of 400 nm to 800 nm. In an embodiment, the method further comprises: determining a third asymmetric optical characteristic value for the other etched profile using a measurement of the other etched profile at the first wavelength; determining a fourth asymmetric optical characteristic value for the other etched profile using a measurement of the other etched profile at the second wavelength; and determining occurrence of tilt in the etching of the other etched profile based on a difference between the third and fourth values. In an embodiment, the optical characteristic values are normalized values.

In association with the physical structures of the targets as realized on substrates and patterning devices, an embodiment may include a computer program containing one or more sequences of machine-readable instructions and/or functional data describing the target design, describing a method of designing a target for a substrate, describing a method of producing a target on a substrate, describing a method of measuring a target on a substrate and/or describing a method of analyzing a measurement to obtain information about a patterning process. This computer program may be executed for example within unit PU in the apparatus of FIG. 7 and/or the control unit LACU of FIG. 2. There may also be provided a data storage medium (e.g., semiconductor memory, magnetic or optical disk) having such a computer program stored therein. Where an existing inspection apparatus, for example of the type shown in FIG. 7, is already in production and/or in use, an embodiment can be implemented by the provision of an updated computer program product for causing a processor to perform one or more of the methods described herein. The program may optionally be arranged to control the optical system, substrate support and the like to perform a method of measuring a parameter of the patterning process on a suitable plurality of targets. The program can update the lithographic and/or metrology recipe for measurement of further substrates. The program may be arranged to control (directly or indirectly) the lithographic apparatus for the patterning and processing of further substrates.

The term "optimizing" and "optimization" as used herein refers to or means adjusting an apparatus and/or process of the patterning process, which may include adjusting a lithography process or apparatus, or adjusting the metrology process or apparatus (e.g., the target, measurement tool, etc.), such that a figure of merit has a more desirable value, such as measurement, patterning and/or device fabrication results and/or processes have one or more desirable characteristics, projection of a design layout on a substrate being more accurate, a process window being larger, etc. Thus, optimizing and optimization refers to or means a process that identifies one or more values for one or more design variables that provide an improvement, e.g. a local optimum, in a figure of merit, compared to an initial set of values of the design variables. "Optimum" and other related terms should be construed accordingly. In an embodiment, optimization steps can be applied iteratively to provide further improvements in one or more figures of merit.

An embodiment of the invention may take the form of a computer program containing one or more sequences of machine-readable instructions describing a method as disclosed herein, or a data storage medium (e.g. semiconductor memory, magnetic or optical disk) having such a computer program stored therein. Further, the machine readable instruction may be embodied in two or more computer programs. The two or more computer programs may be stored on one or more different memories and/or data storage media.

One or more aspects disclosed herein may be implemented in a control system. Any control system described herein may each or in combination be operable when the one or more computer programs are read by one or more computer processors located within at least one component of an apparatus. The control systems may each or in combination have any suitable configuration for receiving, processing, and sending signals. One or more processors are configured to communicate with the at least one of the control systems. For example, each control system may include one or more processors for executing the computer programs that include machine-readable instructions for the methods described above. The control systems may include data storage medium for storing such computer programs, and/or hardware to receive such medium. So the control system(s) may operate according the machine readable instructions of one or more computer programs.

Although specific reference may have been made above to the use of embodiments in the context of optical lithography and etching, it will be appreciated that embodiments of the invention may be used in other applications. For example, embodiments may be with imprint lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured. Further, the embodiments here can be used with any process that causes an asymmetry in the structure and so could be used with, e.g., other material removal processes or with an additive process.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the disclosure have been described above, it will be appreciated that the disclosure may be practiced otherwise than as described. For example, the disclosure may take the form of a computer program containing one or more sequences of machine-readable instructions describing a method as disclosed above, or a data storage medium (e.g. semiconductor memory, magnetic or optical disk) having such a computer program stored therein.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, third party content delivery networks may host some or all of the information conveyed over networks, in which case, to the extent information (e.g., content) is said to be supplied or otherwise provided, the information may be provided by sending instructions to retrieve that information from a content delivery network.

Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device.

The reader should appreciate that the present application describes several inventions. Rather than separating those inventions into multiple isolated patent applications, applicants have grouped these inventions into a single document because their related subject matter lends itself to economies in the application process. But the distinct advantages and aspects of such inventions should not be conflated. In some cases, embodiments address all of the deficiencies noted herein, but it should be understood that the inventions are independently useful, and some embodiments address only a subset of such problems or offer other, unmentioned benefits that will be apparent to those of skill in the art reviewing the present disclosure. Due to costs constraints, some inventions disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such inventions or all aspects of such inventions.

It should be understood that the description and the drawings are not intended to limit the invention to the particular form disclosed, but to the contrary, the intention is to cover all modifications, equivalents, and alternatives falling within the spirit and scope of the present invention as defined by the appended claims.

Modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, certain features may be utilized independently, and embodiments or features of embodiments may be combined, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an" element or "a" element includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every.

To the extent certain U.S. patents, U.S. patent applications, or other materials (e.g., articles) have been incorporated by reference, the text of such U.S. patents, U.S. patent applications, and other materials is only incorporated by reference to the extent that no conflict exists between such material and the statements and drawings set forth herein. In the event of such conflict, any such conflicting text in such incorporated by reference U.S. patents, U.S. patent applications, and other materials is specifically not incorporated by reference herein.

Embodiments are described in the below numbered clauses:
1. A method comprising:
   obtaining a first value of an optical characteristic determined for an etched profile of a substrate measured at a first wavelength of measurement radiation, obtaining a second value of the optical characteristic determined for the etched profile of the substrate measured at a second wavelength of measurement radiation, and obtaining a derived value that represents a difference between the first and second values; and
   determining, by a hardware computer and based on the first and second values or on the derived value, an occurrence of a tilt in the etching to form the etched profile.
2. The method of clause 1, wherein the first and second values are obtained for an etched profile having a structural asymmetry caused due to the tilt in the etching.
3. The method of clause 1 or clause 2, wherein the determining is based on the derived value.
4. The method of any of clauses 1-3, wherein the first and second wavelengths are such that the first and second values are relatively insensitive to variation in depth of etching of the etched profile.
5. The method of clause 4, wherein relatively insensitive means that a change of less or equal to ±20% of the depth of etching yields a change of less than or equal to ±20% of the first and second values.
6. The method of any of clauses 1-5, wherein the optical characteristic is reflectance.
7. The method of any of clauses 1-6, wherein the optical characteristic values comprise asymmetric optical characteristic values obtained by subtracting a value of the optical characteristic for a pupil location from a value of the optical characteristic for a pupil location that is point symmetrically positioned with respect to a point at a central portion of the pupil.
8. The method of clause 7, wherein the first value is a negative value and the second value is positive value, or vice versa.
9. The method of any of clauses 1-8, wherein the optical characteristic values are normalized values.
10. The method of any of clauses 1-9, wherein the tilt in the etching comprises ion beam tilt.
11. The method of any of clauses 1-10, wherein the etched profile has a pitch of about 100 nm or less.
12. The method of any of clauses 1-11, wherein the first and second wavelengths are selected from the range of 400 nm to 800 nm.
13. The method of any of clauses 1-12, wherein the occurrence of tilt in the etching comprises an occurrence a tilt within 5 degrees of perpendicular of a main surface of the substrate.
14. A method, comprising:
   obtaining asymmetric optical characteristic values for an asymmetric etched profile of a substrate at each of a plurality of different wavelengths of measurement radiation, wherein the asymmetry of the etched profile is caused by tilt in the etching and each of the asymmetric optical characteristic values corresponds to a difference between a value of the optical characteristic for a first pupil location and a value of the optical characteristic for a second pupil location that is point symmetrically positioned with respect to a point at a central portion of the pupil; and
   identifying, by a hardware computer and based on the values, a first wavelength of measurement radiation at which a first value of the asymmetric optical characteristic values is negative and a second wavelength of measurement radiation at which a second value of the asymmetric optical characteristic values is positive, wherein occurrence of tilt in the etching of another etched profile can be determined by finding a difference between a value of the asymmetric optical characteristic determined for the other etched profile using a measurement at the first wavelength and a value of the asymmetric optical characteristic determined for the other etched profile using a measurement at the second wavelength.
15. The method of clause 14, wherein the first and second wavelengths are such that the first and second values are relatively insensitive to variation in depth of etching of the etched profile.
16. The method of clause 15, wherein relatively insensitive means that a change of less or equal to ±20% of the depth of etching yields a change of less than or equal to ±20% of the first and second values.
17. The method of any of clauses 14-16, wherein the optical characteristic is reflectance.
18. The method of any of clauses 14-17, wherein the tilt in the etching comprises ion beam tilt.
19. The method of any of clauses 14-18, wherein the first and second wavelengths are selected from the range of 400 nm to 800 nm.
20. The method of any of clauses 14-19, further comprising:
   determining a third asymmetric optical characteristic value for the other etched profile using a measurement of the other etched profile at the first wavelength;
   determining a fourth asymmetric optical characteristic value for the other etched profile using a measurement of the other etched profile at the second wavelength; and
   determining occurrence of tilt in the etching of the other etched profile based on a difference between the third and fourth values.
21. The method of any of clauses 14-20, wherein the optical characteristic values are normalized values.

22. A computer program product comprising a computer non-transitory readable medium having instructions recorded thereon, the instructions when executed by a computer implementing the method of any of clauses 1-21.

23. A system comprising:
  a hardware processor system; and
  a non-transitory computer readable storage medium configured to store machine-readable instructions, wherein when executed, the machine-readable instructions cause the hardware processor system to perform the method of any of clauses 1-21.

24. A system comprising:
  a metrology apparatus configured to provide a beam of radiation onto an object surface and to detect radiation redirected by the object surface; and
  the computer program product of clause 22.

25. The system of clause 24, further comprising a lithographic apparatus comprising a support structure configured to hold a patterning device to modulate a radiation beam and a projection optical system arranged to project the modulated radiation beam onto a radiation-sensitive substrate, wherein the object is the substrate.

26. The system of clause 24, further comprising an etching apparatus configured to etch the object and having a control system configured to process a control signal derived from determination of the occurrence of a tilt in the etching.

27. A metrology apparatus for measuring an object of a patterning process, the metrology apparatus configured to perform the method of any of clauses 1-21.

The foregoing description of the specific embodiments reveals the general nature of embodiments of the invention such that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The descriptions above are intended to be illustrative, not limiting. Thus, it will be apparent to one skilled in the art that modifications may be made to the disclosure as described without departing from the scope of the claims set out below and the breadth and scope of the present invention should not be limited by any of the above-described exemplary embodiments, but should be defined only in accordance with the following claims and their equivalents.

The invention claimed is:

1. A method comprising:
  obtaining a first value of an optical characteristic determined for an etched profile of a substrate measured at a first wavelength of measurement radiation;
  obtaining a second value of the optical characteristic determined for the etched profile of the substrate measured at a second wavelength of measurement radiation;
  obtaining a derived value that represents a difference between the first and second values; and
  determining, by a hardware computer and based on the first and second values or on the derived value, an occurrence of a tilt in the etching to form the etched profile.

2. The method of claim 1, wherein the first and second values are obtained for an etched profile having a structural asymmetry caused due to the tilt in the etching.

3. The method of claim 1, wherein the determining is based on the derived value.

4. The method of claim 1, wherein the first and second wavelengths are such that the first and second values are relatively insensitive to variation in depth of etching of the etched profile.

5. The method of claim 4, wherein relatively insensitive means that a change of less than or equal to ±20% of the depth of etching yields a change of less than or equal to ±20% of the first and second values.

6. The method of claim 1, wherein the optical characteristic is reflectance.

7. The method of claim 1, wherein the optical characteristic values comprise asymmetric optical characteristic values obtained by subtracting a value of the optical characteristic for a pupil location from a value of the optical characteristic for a pupil location that is point symmetrically positioned with respect to a point at a central portion of the pupil.

8. The method of claim 7, wherein the first value is a negative value and the second value is a positive value, or vice versa.

9. The method of claim 1, wherein the optical characteristic values are normalized values.

10. The method of claim 1, wherein the tilt in the etching comprises ion beam tilt.

11. The method of claim 1, wherein the etched profile has a pitch of about 100 nm or less.

12. The method of claim 1, wherein the first and second wavelengths are selected from the range of 400 nm to 800 nm.

13. The method of claim 1, wherein the occurrence of tilt in the etching comprises an occurrence of a tilt within 5 degrees of perpendicular of a main surface of the substrate.

14. A computer program product comprising a non-transitory computer readable medium having instructions recorded thereon, the instructions configured to cause a computer system to at least:
  obtain a first value of an optical characteristic determined for an etched profile of a substrate measured at a first wavelength of measurement radiation,
  obtain a second value of the optical characteristic determined for the etched profile of the substrate measured at a second wavelength of measurement radiation,
  obtain a derived value that represents a difference between the first and second values; and
  determine, based on the first and second values or on the derived value, an occurrence of a tilt in the etching to form the etched profile.

15. A system comprising:
  a hardware processor system; and
  the computer program product of claim 14.

16. A system comprising:
  a metrology apparatus configured to provide a beam of radiation onto an object surface and to detect radiation redirected by the object surface; and
  the computer program product of claim 14.

17. The system of claim 16, further comprising a lithographic apparatus comprising a support structure configured to hold a patterning device to modulate a radiation beam and a projection optical system arranged to project the modulated radiation beam onto a radiation-sensitive substrate, wherein the object is the substrate.

18. The system of claim 16, further comprising an etching apparatus configured to etch the object and having a control system configured to process a control signal derived from determination of the occurrence of a tilt in the etching.

19. A metrology apparatus configured to measure an object of a patterning process, the metrology apparatus comprising the computer program product of claim 14.

* * * * *